United States Patent
Piccirillo

(10) Patent No.: US 11,039,830 B2
(45) Date of Patent: Jun. 22, 2021

(54) ADJUSTABLE LOOP WITH LOCKING KNOT

(71) Applicant: DePuy Synthes Products LLC, Raynham, MA (US)

(72) Inventor: Justin Piccirillo, Uxbridge, MA (US)

(73) Assignee: Medos International Sarl, Le Locle (CH)

( * ) Notice: Subject to any disclaimer, the term of this patent is extended or adjusted under 35 U.S.C. 154(b) by 273 days.

(21) Appl. No.: 16/033,549

(22) Filed: Jul. 12, 2018

(65) Prior Publication Data
US 2020/0015810 A1    Jan. 16, 2020

(51) Int. Cl.
  *A61B 17/06* (2006.01)
  *A61B 17/04* (2006.01)

(52) U.S. Cl.
  CPC .... *A61B 17/06166* (2013.01); *A61B 17/0401* (2013.01); *A61B 2017/0618* (2013.01); *A61B 2017/06185* (2013.01)

(58) Field of Classification Search
  CPC ...... A61B 17/0401; A61B 2017/06185; A61B 17/06166; A61B 2017/0464; A61B 2017/0496; A61B 2017/0475; A61B 2017/0474; A61B 2017/0477; A61B 17/0466; A61B 2017/0618; A61B 2017/0446; A61B 2017/0462; A61F 2002/0852
  See application file for complete search history.

(56) References Cited

U.S. PATENT DOCUMENTS

| | | | |
|---|---|---|---|
| 4,705,040 | A | 11/1987 | Mueller et al. |
| 5,628,756 | A | 5/1997 | Barker |
| 6,030,007 | A | 2/2000 | Bassily et al. |
| 6,972,027 | B2 | 12/2005 | Fallin et al. |
| 8,790,370 | B2 | 7/2014 | Spenciner et al. |
| 9,060,763 | B2 | 6/2015 | Sengun |
| 9,095,331 | B2 | 8/2015 | Hernandez et al. |
| 9,345,468 | B2 | 5/2016 | Sengun et al. |
| 2006/0064126 | A1 | 3/2006 | Fallin et al. |
| 2012/0245629 | A1 | 9/2012 | Gross et al. |

(Continued)

FOREIGN PATENT DOCUMENTS

EP    3228256 A2    10/2017

OTHER PUBLICATIONS

Partial European Search Report for Application No. EP19185715.0 dated Nov. 19, 2019 (16 pages).

*Primary Examiner* — Katrina M Stransky

(57) ABSTRACT

Systems, devices, and methods for soft tissue repair are generally provided and they generally involve the use of surgical filaments that are configured in a variety of manners to minimize and/or eliminate the tying of knots during a surgical procedure. Moreover, systems and devices described herein can provide for a reversible locking knot, which allows for additional tension to be applied to the repair if adjustments are required after the construct has been locked. The reversible locking knot can be "flipped" or actuated without requiring the knot to be untied and then retied. Further, systems and devices described herein can additionally be used to associate implantable bodies and suture constructs within a bone to secure soft tissue while not restricting the relative movements of operative sutures once the implantable body has been deployed.

30 Claims, 19 Drawing Sheets

(56) References Cited

U.S. PATENT DOCUMENTS

| | | |
|---|---|---|
| 2013/0296895 A1* | 11/2013 | Sengun .............. A61B 17/0401 606/148 |
| 2013/0296931 A1 | 11/2013 | Sengun |
| 2014/0330312 A1 | 11/2014 | Spenciner et al. |
| 2015/0164497 A1 | 6/2015 | Callison et al. |
| 2016/0000421 A1 | 1/2016 | Larsen |
| 2018/0353167 A1* | 12/2018 | Lombardo ....... A61B 17/06166 |

* cited by examiner

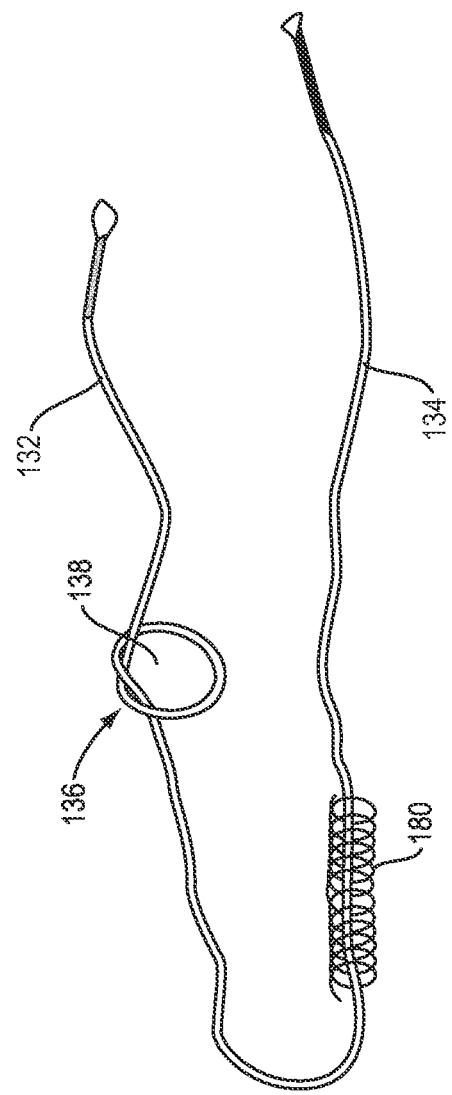

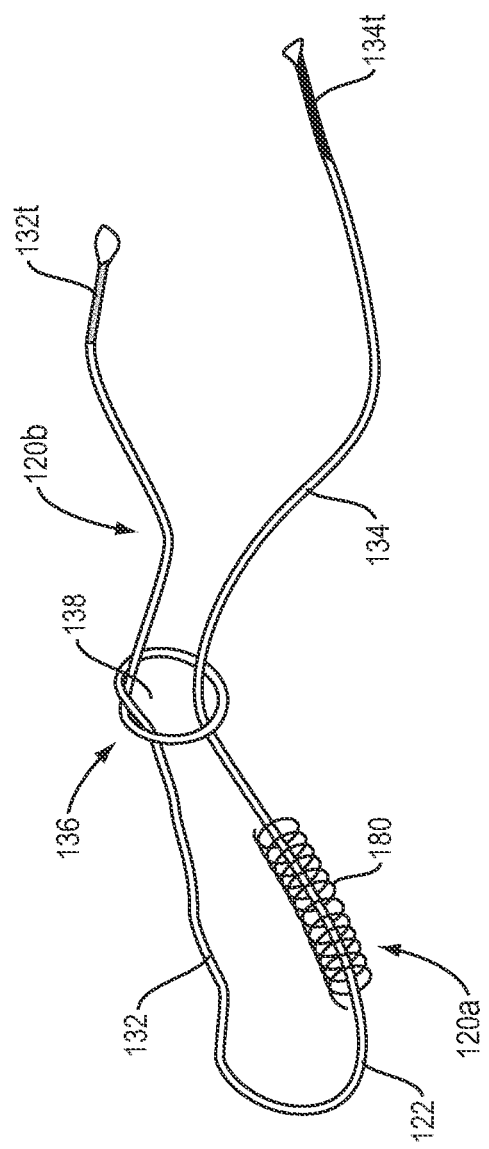

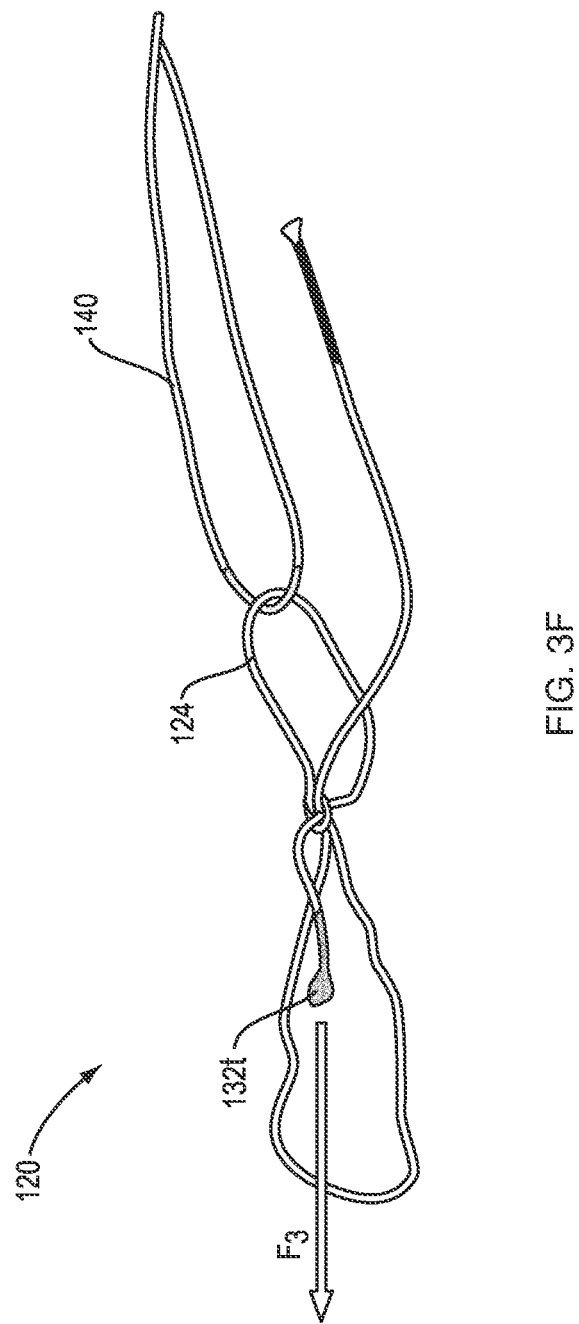

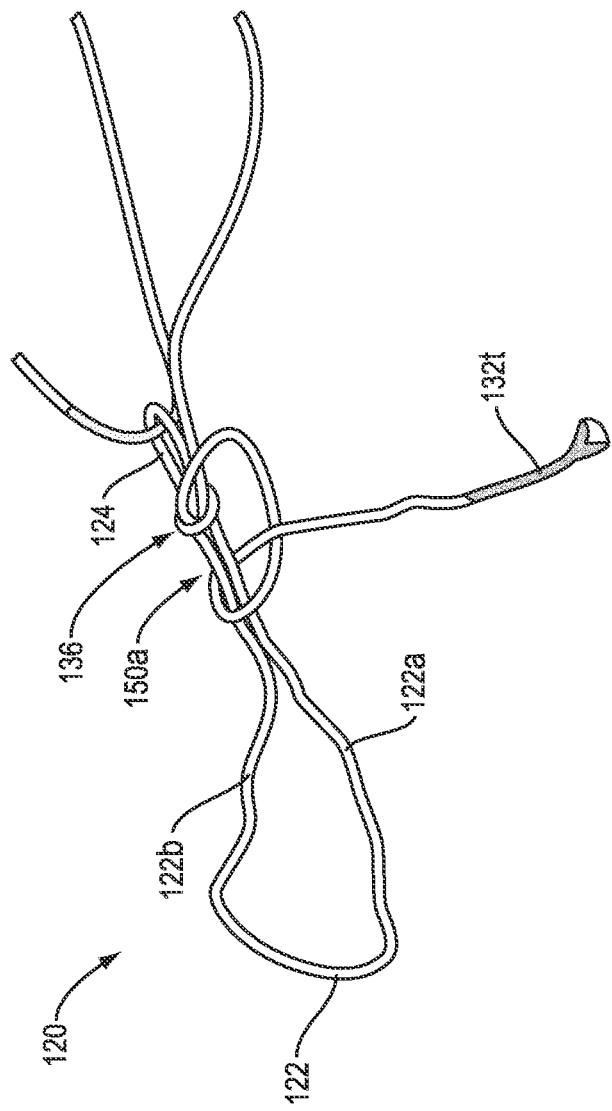

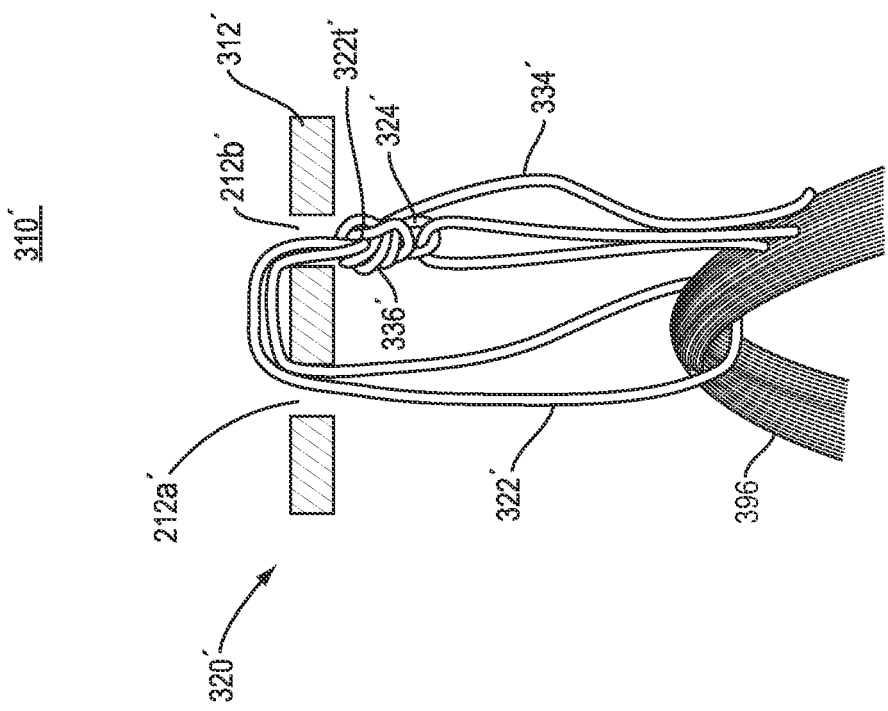
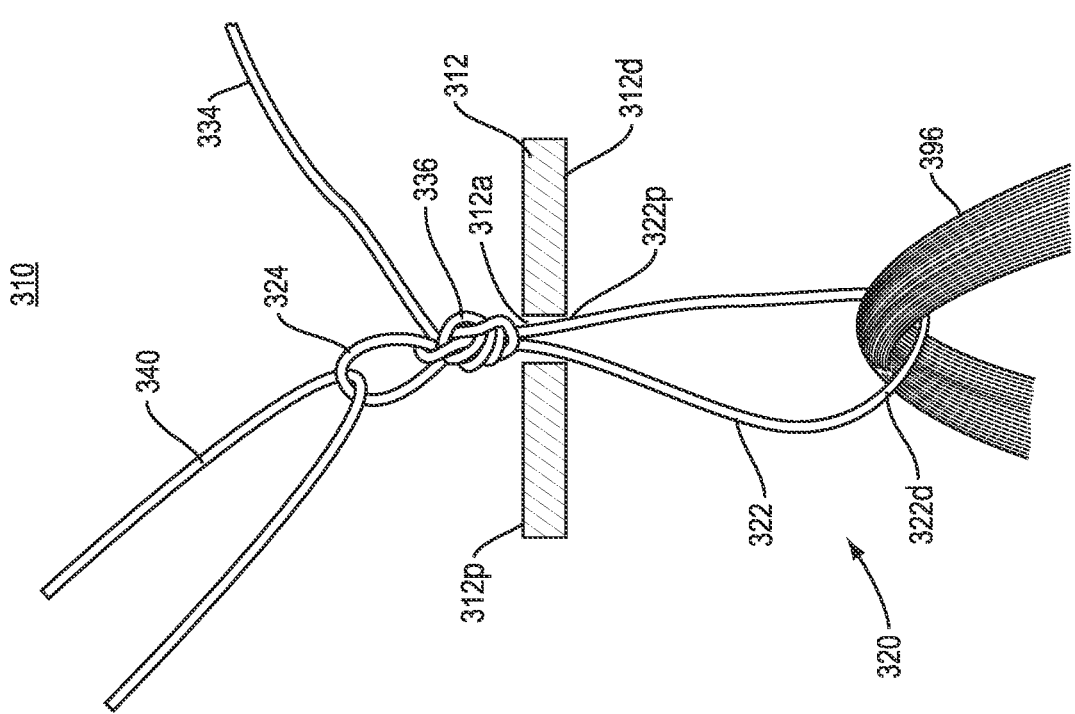
FIG. 8B
FIG. 8A

ADJUSTABLE LOOP WITH LOCKING KNOT

FIELD

The present disclosure relates to systems, devices, and methods for securing soft tissue to bone, and more particularly a suture construct that includes a self-locking knot, a selectively adjustable loop, and a fixed eyelet.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Further, currently available devices for patients of advancing age can be particularly insufficient due to soft and weak bones leading to inadequate suture-to-anchor fixation.

During tissue repair procedures, such as shoulder rotator cuff and instability procedures, arthroscopic knot tying is a common practice. In some common procedures, an anchor loaded with suture is first disposed in bone. The suture is normally slidably attached to the anchor through an eyelet or around a post or similar feature such that a single length of suture has two free limbs extending from the anchor. One limb of the suture can then be passed through soft tissue to be repaired (e.g., tendon, labrum). The two ends of the suture can then be tied to each other, thereby capturing the soft tissue in a loop with the anchor. The loop can be subsequently collapsed to draw the tissue towards the anchor, and thus the bone.

Surgeons often use a surgical sliding knot, such as a Tennessee Slider or a Duncan Loop, to tie the suture ends together to form the loop. A force can then be imparted on the sliding knot to advance it towards the bone, which, in turn, collapses the loop to draw the tissue towards the anchor and the bone. Once the knot, and thus the tissue, is at a desired location with respect to the anchor and bone, the location of the knot can be fixed in place using techniques known to those skilled in the art. For example, one customary way to secure the location of the knot is to tie a number of half hitches or other knots on the suture, proximate to the knot, to hold the location of the knot. Such a configuration can prevent the knot from loosening or sliding. If knots are not formed, a conventional sliding knot does not typically provide appropriate protection against loosening or slippage, especially when tension is placed primarily on the limbs of the loop. In some instances, a surgeon may at least form three reversed half hitches on alternating posts or limbs of the suture, proximate to the knot, to prevent the knot from loosening or slipping.

A person skilled in the art, however, will recognize that even before one or more half hitches or the like are formed proximate to the sliding knot, there exists a potential for the sliding knot to slip, causing the loop to enlarge and the desired location of the tissue be lost. This has been referred to as loss of "loop security," and can reportedly occur even in the hands of very experienced surgeons. Sometimes, even fully-tied knots may slip. Still further, in addition to "loop security" issues, many conventional knots can have an overall size that may be obstructive or intrusive, especially in tight joints, which may damage cartilage or other tissue by abrasion with the knot.

The types of anchors used in conjunction with the aforementioned types of tissue repairs include both soft anchors, which are often made out of filament or similar materials, as well as more traditional hard anchors. Non-limiting examples of some such soft and hard anchors are provided below in the detailed description either by being described or being incorporated by reference, and many different configurations of the same are known to those skilled in the art.

Whether using hard or soft anchors, some steps often involved in a repair process can include: (1) securing an anchor at a desired location with respect to bone to which tissue is to be attached (e.g., within or adjacent to a bore in a bone); (2) associating one or more operative and/or accessory suture(s) that are in some manner coupled to the anchor with the tissue to be attached to bone; (3) sliding or otherwise manipulating one or more of the operative and/or accessory suture(s) to perform a repair procedure that results in tensioning the tissue to draw the tissue to a desired location with respect to the bone; (4) securing the repair, including the tensioned tissue, at the desired location with respect to the bone; and (5) removing operative and/or accessory sutures from the surgical site as appropriate. When the anchor is a soft anchor, the step of securing an anchor at a desired location can include deploying an anchor, such as by expanding or otherwise actuating the anchor. While some of the aforementioned steps, or other steps performed during a repair procedure, may be able to performed simultaneously, it can often be desirable to separate each step, and their related functional outputs, so that suture(s) and other components of the repair (e.g., the anchor, tissue, etc.) do not get trapped, caught, become difficult to maneuver, etc.

A number of other complications also exist with respect to current tissue repair procedures. For example, it is desirable to minimize a size of the components being implanted in the body (e.g., the anchor, the suture(s), etc.). Further, existing suture implant systems can require substantial forces, on the order of about 40 pounds of force to about 50 pounds of force, to fully insert implants (e.g., anchors), which can increase the difficulty of soft tissue repair procedures, for instance, by putting undesirable stress on tissue, bone, etc. Still further, some existing implant systems often require the use of one or more sutures that are not easily removed from the surgical site after completion of procedure even though the suture(s) is not functionally holding any tissue, bone, or key part of the system in place. Yet another complication with existing systems is that some systems are not versatile such that they can allow a user to reverse actions once taken. For example, in some systems, once a suture loop has been collapsed and/or locked into a location, there is no easy way to expand the loop and/or unlock its location.

Accordingly, there is a need for systems, devices, and methods for use in soft tissue repair that are robust and strong, yet minimize or eliminate the number and size of knots to be tied by a surgeon, particularly during arthroscopic repair procedures. There is also a need for systems, devices, and methods that reduce the amount of force needed to secure the location of an implant with respect to a bone while keeping the location of the implant, suture, and related tissue as secure as possible. There is a further need for systems, devices, and methods that provide enhanced maneuverability, adjustability, versatility, and selective locking of a suture construct and its related components.

SUMMARY

Systems, devices, and methods for soft tissue repair are generally provided and they involve the use of surgical filaments that are configured in a variety of manners to minimize and/or eliminate the tying of knots during a surgical procedure. The systems and devices described herein provide superior strength for use in a number of different surgical procedures, such as rotator cuff and instability repair procedures, and other types of tendon and tissue repair procedures. They also allow for attachments that have a lower profile than existing systems and devices, which allows for the filaments to become associated with tissue, for instance by passing the filaments through the tissue or wrapping the filaments around the tissue, with minimal trauma to the tissue and less space being taken up by the overall construction. This results in systems and devices that can be associated with tissue atraumatically to secure the tissue in a knotless manner.

Moreover, systems and devices described herein provide for a reversible locking knot (the knot often being pre-tied such that a surgeon does not have to tie the knot during a procedure), which can allow for additional tension to be applied to the repair if adjustments are required after the construct has been locked. The reversible locking knot can be "flipped" or actuated without requiring the knot to be untied and then retied. More particularly, the reversible locking knot allows an associated collapsible loop to be selectively locked and unlocked. As provided for herein, when the reversible locking knot is in an unlocked position, the collapsible loop can have a size of an opening defined by the loop adjusted, i.e., a diameter of the collapsible loop can be made bigger and smaller. When the reversible locking knot is in a locked position, the size of the opening defined by the collapsible loop can be maintained, i.e., the diameter of the loop is fixed. Further, systems and devices described herein can additionally be used to associate implantable bodies (e.g., anchors) and suture constructs within a bone to secure soft tissue while not restricting the relative movements of operative sutures once the implantable body has been deployed or otherwise positioned with respect to bone.

In one exemplary embodiment of a suture construct, the construct includes a filament loop having a slidable knot, an adjustable limb and a fixed loop that each extend from the slidable knot, and an implantable body coupled to the filament loop. The filament loop defines an opening that has an adjustable diameter, and the adjustable limb is configured to adjust the adjustable diameter of the opening when tension is applied to the adjustable limb to move the adjustable limb with respect to the slidable knot. The fixed loop also defines an opening, but the opening has a fixed diameter. Further, the fixed loop has a first, unlocked configuration and a second locked configuration. When the fixed loop is in the first, unlocked configuration, the adjustable limb is movable with respect to the slidable knot and the adjustable diameter of the filament loop is adjustable. When the fixed loop is in the second, locked configuration, the adjustable limb is prevented from moving with respect to the slidable knot such that the adjustable diameter of the filament loop is fixed.

In some embodiments, a single filament can be used to form the filament loop, the adjustable limb, and the fixed loop. The implantable body can have a variety of configurations. For example, the implantable body can include a filament (e.g., a soft anchor, as provided for herein or otherwise known to those skilled in the art). Alternatively, or additionally, the implantable body can include at least one cortical button. In some such embodiments, there can include two cortical buttons.

The fixed loop can be rotatable with respect to the slidable knot such that rotation of the fixed loop with respect to the slidable knot moves the fixed loop from the first, unlocked configuration to the second, locked configuration. The second, locked configuration can be reversible such that the fixed loop can be moved from the second, locked configuration to the first, unlocked configuration. The adjustable limb can pass through the slidable knot. It can have a substantially straight configuration within the slidable knot when the fixed loop is in the first, unlocked configuration, and a tortious configuration within the slidable knot when the fixed loop is in the second, locked configuration.

One exemplary embodiment of an implant includes a soft anchor that is configured to be fixed in bone and is formed of a flexible construct, a filament that extends from the soft anchor, and a suture attachment loop that is formed from the filament. The soft anchor has an unstressed configuration with a first length and a first diameter and an anchoring configuration with a second length and a second diameter. The second length is less than the first length, and the second diameter is greater than the first diameter. The filament that extends from the suture anchor is configured to apply tension to the soft anchor to move it from the unstressed configuration to the anchoring configuration, and the suture attachment loop defines an opening that has a fixed diameter configured to receive a suture through the opening.

The suture attachment loop can be configured to slidably receive suture through it. The filament can include a locking knot. The locking knot can be configured such that it has a first configuration in which the locking knot permits the soft anchor to be adjusted and a second configuration in which the locking knot locks the configuration of the soft anchor. In some embodiments, the filament can include an adjustable anchor loop. In some such embodiments, the soft anchor can be disposed on the adjustable anchor loop and the filament extending from the soft anchor can be configured to adjust the diameter of the adjustable anchor loop.

One exemplary embodiment of a method of using a suture repair construct includes tying a first limb of a suture repair construct about a portion of an adjustable loop of the suture repair construct to set a size of an opening defined by an eyelet of the suture repair construct. The size of the opening defined by the eyelet is adjustable prior to tying the first limb of the suture repair construct about the portion of the adjustable loop. The method further includes tying the eyelet about a second limb of the suture repair construct to form a lockable knot, with the second limb of the suture repair construct being operable to control a size of an opening defined by the adjustable loop. The second limb is configured to slide within the lockable knot after the eyelet is tied about the second limb.

The method can further include disposing an operative suture in the eyelet such that a portion of the operative suture is disposed on opposed side of the eyelet, and manipulating the operative suture to tie the eyelet about the second limb of the suture repair construct to form the lockable knot. In some embodiments, the method can include tensioning the first limb of the suture repair construct to collapse the size of the opening defined by the eyelet prior to tying the first limb of the suture repair construct about a portion of the adjustable loop to set a size of the opening defined by the eyelet. The method can also include tensioning the second limb of the suture repair construct to collapse the size of the opening defined by the adjustable loop after tying the eyelet about the second limb to form the lockable knot.

In some embodiments, the method can include coupling the suture repair construct to a suture anchor. Many different types of anchors can be used, but in some such instances, the anchor can include a soft anchor that is configured to be fixated in bone and can be formed of a flexible construct. The soft anchor can have an unstressed configuration with a first length and a first diameter and an anchoring configuration with a second length and a second diameter. The second length can be less than the first length and the second diameter can be greater than the first diameter. In some such embodiments, the method can include inserting the soft anchor in a bone, threading at least a portion of the operative suture through a portion of tissue, tensioning the second limb to move the anchor from the first configuration to the second configuration, and tensioning the eyelet to move the lockable knot from a first, unlocked configuration to a second locked configuration. Many different results can be achieved by tensioning the eyelet to move the lockable knot from the first, unlocked configuration to the second, locked configuration, including, by way of non-limiting example, causing a tendon coupled to the adjustable loop of the suture repair construct to be substantially fixed at a desired location. The method can further include manipulating the eyelet to move the lockable knot from the second, locked configuration to the first, unlocked configuration. Many different results can be achieved by manipulating the eyelet to move the lockable knot from second, locked configuration to the first, unlocked configuration, including, by way of non-limiting example, allowing a diameter of the adjustable loop of the suture repair construct to be adjusted after previously having been fixed when in the locked configuration.

One exemplary method for manufacturing a suture construct involves using a single piece of suture that has a first terminal end and a second terminal end. The method includes forming an overhand knot on a limb of the single piece of suture, with the overhead knot being in an uncollapsed configuration such that an opening is formed by the limb, and inserting the second terminal end of the suture through the opening of the overhand knot to create a sliding loop. The method further includes inserting the first end of the suture through the opening to form an eyelet, and collapsing the overhand knot such that each of the sliding loop, the eyelet, the first end, and the second end extend from the collapsed overhand knot. In the resulting configuration, a size of the sliding loop is adjustable by the second end and the size of the eyelet is adjustable by the first end.

In some embodiments, the method can include tying a half-hitch knot around a portion of the single piece of suture with the eyelet to form a lock. The lock can be configured such that upon actuation of the lock, a size of an opening defined by the sliding loop is fixed. The method can also include threading a soft anchor onto the sliding loop.

BRIEF DESCRIPTION OF DRAWINGS

FIGS. 3A-E schematically illustrate one exemplary embodiment for manufacturing a suture construct;

FIGS. 3F-3K schematically illustrate one exemplary embodiment of a method of manipulating the suture construct of FIG. 3E in conjunction with an operative suture;

FIG. 8A is another exemplary embodiment of an implant having one exemplary suture construct associated therewith;

FIG. 8B is yet another exemplary embodiment of an implant having one exemplary suture construct associated therewith.

DETAILED DESCRIPTION

Figure 2:
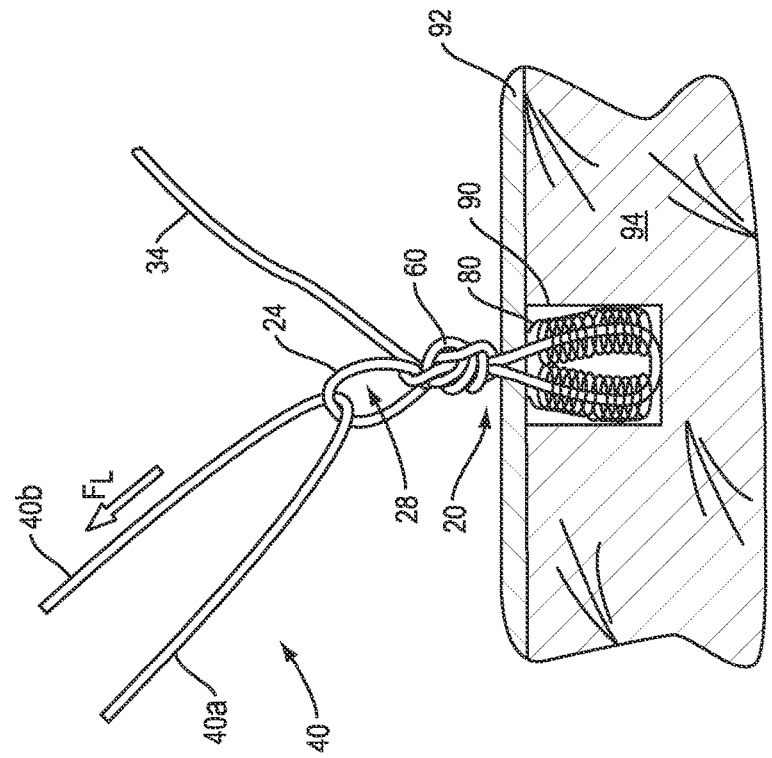
FIG. 2 is a side view of the suture construct of FIG. 1 in an implant configuration.

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features, and thus within a particular embodiment each feature of each like-numbered component is not necessarily fully elaborated upon. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction a component can be tensioned or pulled, these arrows are illustrative and in no way limit the direction the respective component can be tensioned or pulled. A person skilled in the art will recognize other ways and directions for creating the desired tension. Likewise, while in some embodiments movement of one component is described with respect to another, a person skilled in the art will recognize that other movements are possible. By way of non-limiting example, in embodiments in which a filament is passed through itself to form a sliding post, movement described with respect to the inner portion (i.e., the sliding post as discussed herein) moving relative to the outer portion can likewise involve movement of the outer portion with respect to the inner portion. As provided for herein, a size of an opening defined by a collapsible loop is sometimes described as having a diameter. A person skilled in the art will recognize that just because the term "diameter" is used to describe a loop, it does not mean that the loop has a fully circular shape. Because suture used to form the loop is flexible, the loop can take on a variety of shapes that may or may not be circular in nature. Accordingly, use of the term "diameter" by no means limits a shape of a collapsible loop and/or an opening defined by the collapsible loop. To the extent the present disclosure describes that a diameter increases or decreases, it merely is reflecting the fact that a size of the opening has changed and that an area defined by that loop has increased or decreased, respectively. Additionally, a number of terms may be used throughout the disclosure interchangeably but will be understood by a person skilled in the art. By way of non-limiting example, the terms suture and filament may be used interchangeably.

Systems, device, and methods for soft tissue repair are provided that allow for added strength and versatility, without adding unnecessary bulk, to the repair construct. More particularly, the present disclosures are directed to a suture repair construct that includes a variety of features formed along the construct. These features include an adjustable loop that can be selectively collapsed to perform tasks like drawing tissue towards bone, an adjustable sliding-locking knot that helps form the adjustable loop, and an eyelet having a fixed diameter, but being configured to be manipulated (also described as "flipped" herein) to move from a position in which it sets a location of the adjustable sliding-locking knot, and thereby fixes a size of an opening of the adjustable loop, and a position in which it allows the adjustable sliding-locking knot to be moved, and thereby allowing a size of the opening of the adjustable loop to be moved. Notably, the ability to selectively unlock and lock the eyelet, and thus the adjustable sliding-locking knot and the adjustable loop, allows for selective adjustments to the location of portions of the construct and/or the tissue with respect the bone without having to untie, tie, and/or retie a knot. In some instances, the suture repair construct may be formed from a single suture or filament, although multiple suture or filaments can also be used. The suture repair construct itself can be coupled to a suture anchor and then used in conjunction with a suture repair procedure. Suture anchors of most any type can be used in conjunction with the disclosure suture repair construct, including hard anchors and soft anchors. The present disclosures provide the benefits of enhanced versatility and strength, while also not restricting the relative movements of suture associated with the overall system and repair.

Figure 1:
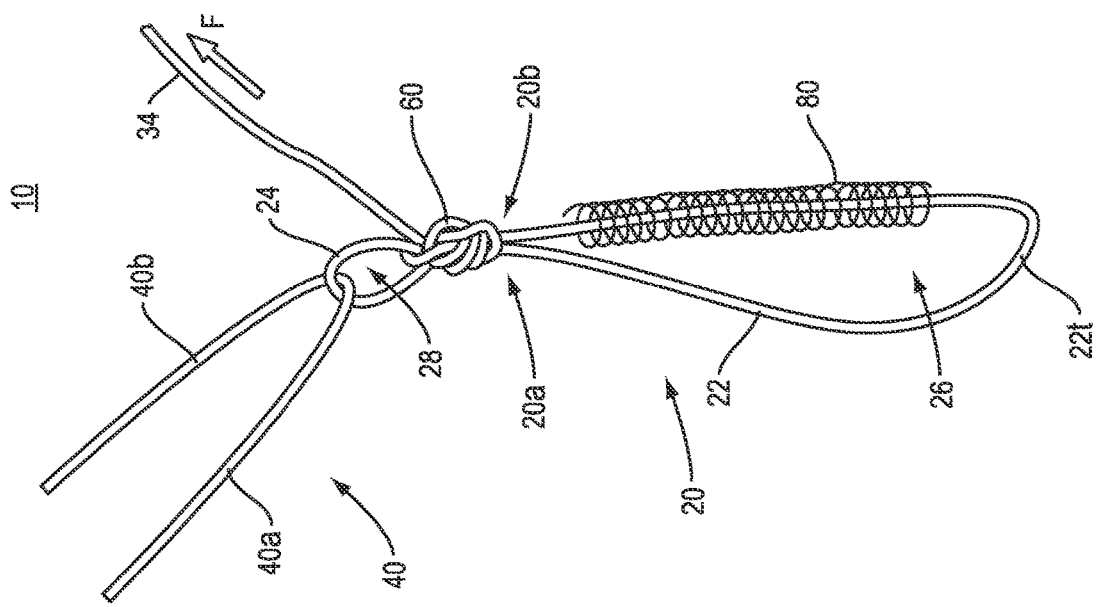
FIG. 1 is a side view of one exemplary embodiment of a suture construct.

FIG. 1 provides one exemplary embodiment of an implant 10 having a suture construct 20, the suture construct 20 having a separate, operative suture 40 associated therewith. The construct 20 is a single length of filament or suture extending between two terminal ends 20a, 20b, also referred to as a limb of suture, with the filament being manipulated to have operative elements formed on or otherwise associated with the filament. The illustrated operative elements of the construct 20 include a filament loop or selectively adjustable loop 22, a fixed loop or eyelet 24, and an adjustable sliding-locking knot 60. As shown, each of these operative elements are formed from the same filament, although, as discussed below, the suture construct 20 can be formed from a plurality of sutures, in which case the operative elements may or may not be formed from the same filament.

The selectively adjustable loop 22 is defined, at least in part, by the adjustable sliding-locking knot 60. As shown, the loop 22 forms an opening 26 having a diameter that can be adjusted. More particularly, application of a force in a direction F to a post 34 of the filament can collapse a size of the opening 26 of the loop 22, i.e., its diameter. In the illustrated embodiment, applying a force in the direction F to the post 34 causes the filament to slide with respect to the adjustable sliding-locking knot 60 in the direction F, thereby decreasing a size of the opening 26, i.e., shrinking its diameter. In some embodiments, the adjustable sliding-locking knot 60 can be moved to adjust the size of the opening 26. For example, the configuration can be such that applying a force in an approximately opposite direction to the direction F can cause the knot 60 to advance in that opposite direction, towards a distal terminal end 22t of the loop 22 as shown, to collapse a size of the opening 26. In some configurations, applying a force in the direction F to the post 34 of the filament can cause the knot 60 to advance in the aforementioned opposite direction, towards the distal terminal end 22t of the loop 22, in a ratchet-like or incremental manner. A person skilled in the art will recognize a number of ways by which the selectively adjustable loop 22 can have the size of its opening 26 adjusted, including increasing its size if desired.

The eyelet 24 is also defined, at least in part, by the adjustable sliding-locking knot 60. As shown, the eyelet 24 extends in a direction approximately opposite to the direction the adjustable loop 22 extends from the adjustable sliding-locking knot. While the formation of the eyelet 24 is described in greater detail with respect to FIGS. 3A-3E, generally the filament that is used to form the eyelet 24 can be manipulated so that an opening 28 defined by the eyelet 24 has a desired size, also referred to as a diameter of the eyelet 24, and then that size is fixed so that it cannot be easily adjusted during use of the construct 20 during some types of procedures. Prior to fixing a size of the opening 28 of the eyelet 24, the diameter of the eyelet 24 can be adjusted. In the illustrated embodiment of FIG. 1, the eyelet 24 is in a locked configuration such that the size of the opening 28 cannot be easily adjusted. More particularly, the sliding-locking knot 60 is formed in a manner that both sets a size of the diameter of the eyelet 24 while also allowing the post 34 to be manipulated to change a size of the diameter of the adjustable loop 22.

An operative or accessory suture 40 can be threaded through the eyelet 24 such that the operative suture is freely slidable relative to the construct 20. While the operative suture 40 can be coupled to other otherwise associated with the construct 20, typically via the eyelet 24, in a number of manners, in the illustrated embodiment a first terminal end 40a of the operative suture 40 is disposed on one side of the eyelet 24 and a second terminal end 40b of the operative suture 40 is disposed on an opposite side of the eyelet 24 with a portion of the suture 40 disposed between the terminal ends 40a, 40b passing through the eyelet 24. As described in greater detail below, and as also known by those skilled in the art, the operative suture 40 can be used to perform one or more of a variety of tasks during any number of surgical procedures, including but not limited to manipulating any of the implant 10, the suture construct 20, and/or an anchor 80 associated therewith to position any of them in desired locations, to secure tissue to desired locations, to adjust their configurations in desired manners, etc.

While the suture construct 20 can be used as a stand-alone implant, in the illustrated embodiment the implant 10 includes an anchor 80 associated with the suture construct 20. More particularly, the anchor 80 is coupled to the selectively adjustable loop 22 so that the anchor 80 and construct 20 can be used together to secure tissue to bone, or to perform other types of repairs made possible by the present disclosures. As shown, the anchor 80 is a soft anchor that is threaded onto the adjustable loop 20 using techniques known to those skilled in the art (e.g., passing the loop 22 through the anchor 80, forming the anchor 80 onto the loop 22, etc.). Soft anchors are generally flexible in nature and can be formed from a flexible filament or from a polymeric material in the form of, for example, a sleeve. Such soft anchors, which typically are non-metallic, can include one or more openings to allow at least a portion of the adjustable loop 22 to pass into and/or through the anchor. Soft anchors can have an unsettled or unstressed configuration, as shown in FIG. 1, which can be used for deployment to the surgical site, and an anchoring configuration, as shown in FIG. 2, which can be used for fixating the anchor following deployment at the surgical site. As further illustrated in FIG. 2, the construct 20 can be locked within the bore by reducing the diameter of the adjustable loop 22 to expand the anchor 80 and the knot 60 can be locked to fix the configuration of the anchor 80. Ways by which the knot 60 can be locked are described in greater detail below.

In the illustrated embodiment, the soft anchor 80 can be moved from the unstressed configuration to the anchoring configuration by applying force in the direction F on the post 34 to collapse the adjustable loop 22, which in turn can cause the soft anchor 80 to actuate from the unstressed configuration to the anchoring configuration, as shown between FIGS. 1 and 2. A person skilled in the art, in view of the present disclosures, will understand a variety of other ways by which the soft anchor 80 can be advanced to the anchoring configuration to set its position with respect to a bone. The transition of a soft anchor from the unstressed configuration to the anchoring configuration typically alters the dimensions of the anchor, such as a length and/or diameter of the anchor. By way of a non-limiting example, a diameter of a soft anchor in its anchoring configuration, which may also be referred to as a second or actuated diameter of the soft anchor, can be approximately in the range of about 10% greater to about 80% greater than the diameter in the unstressed configuration, which may also be referred to as a first or initial diameter. In one embodiment, the second diameter can be about 20% greater than the first diameter of the soft anchor. Similarly, by way of further non-limiting example, a length of a soft anchor in its anchoring configuration, which may also be referred to as a second or actuated length, can be approximately in the range of about 20% less to about 80% less than a length of the soft anchor in its unstressed configuration, which may also be referred to as a first or initial length. In one embodiment the second length can be about 50% less than the first length.

Many different types and configurations of soft anchors can be used in lieu of the soft anchor 80. A person skilled in the art, in view of the present disclosures, will recognize many other feasible soft anchors that can be used in conjunction with the suture construct 20, and the other suture constructs provided for herein (e.g., constructs 120, 220, 220', 320) or otherwise derivable from the present disclosures. Some non-limiting examples of such soft suture anchors are described in U.S. Pat. No. 9,345,567 to Sengun, the content of which is incorporated by reference herein in its entirety. Likewise, all types of hard anchors may also be used in lieu of the soft anchor 80. A person skilled in the art will recognize the many different types of hard anchors that exist and can be used in conjunction with the present disclosures, and thus a more elaborate description of such anchors is unnecessary. Further, while this paragraph describes that other soft and hard anchors can be used in lieu of the soft anchor 80, a person skilled in the art, in view of the present disclosures, will understand ways by which multiple anchors can be used in conjunction with one or more suture constructs (e.g., the constructs 20, 120, 220, 220', and 320), without departing from the spirit of the present disclosure, and thus other soft and hard anchors can also be used in conjunction with the soft anchor 80 if desired.

The suture construct 20 and the operative suture 40, as well as other suture constructs and other sutures provided for herein or otherwise derivable from the present disclosure, can be made of any suitable flexible material, for instance a filament, including a cannulated filament, a braided filament, and a mono filament. The type, size, and strength of the flexible material can depend, at least in part, on the type of anchor with which it is used, any obstructions through which the suture construct may pass, and the type of procedure in which it is used. In one exemplary embodiment the flexible material is a #2 filament (about 23 gauge to about 24 gauge), such as an Orthocord™ filament that is commercially available from DePuy Synthes or Ethibond™ filament available from Ethicon, Inc. Generally the filament is relatively thin to minimize any trauma to tissue through which it passes. In some embodiments the filament can have a size between about a #5 filament (about 20 gauge to about 21 gauge) and about a #5-0 filament (about 35 gauge to about 38 gauge). The Orthocord™ #2 filament can be useful because it has a braided configuration, which allows other components, including the filament itself, to pass through subcomponents of the braid without causing damage to the filament. Filaments configured to allow for a cannulated configuration, such as by removing a core therefrom or having a preformed cannulated configuration, can also be used. Orthocord™ suture is approximately fifty-five to sixty-five percent PDS™ polydioxanone, which is bioabsorbable, and the remaining thirty-five to forty-five percent ultra-high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. Further, a length of filaments used to form the suture construct 20 can be in the range of about 15 centimeters to about 125 centimeters, and in one embodiment it can be about 60 centimeters.

A person having skill in the art will recognize that the configurations of the present disclosure are just some options for forming suture constructs. In the illustrated embodiment the suture construct 20 is made of a single filament. In other embodiments, however, multiple filaments can be used, for example by using one filament to create a selectively adjustable loop and another filament to form a fixed eyelet. Further, the type of filament(s) used to form one part of the implant and/or construct does not have to be the same type throughout the entire implant and/or construct. By way of non-limiting example, the type of filament used to form the construct 20 can be different than the type of filament used for the operative suture 40.

Figure 3A:
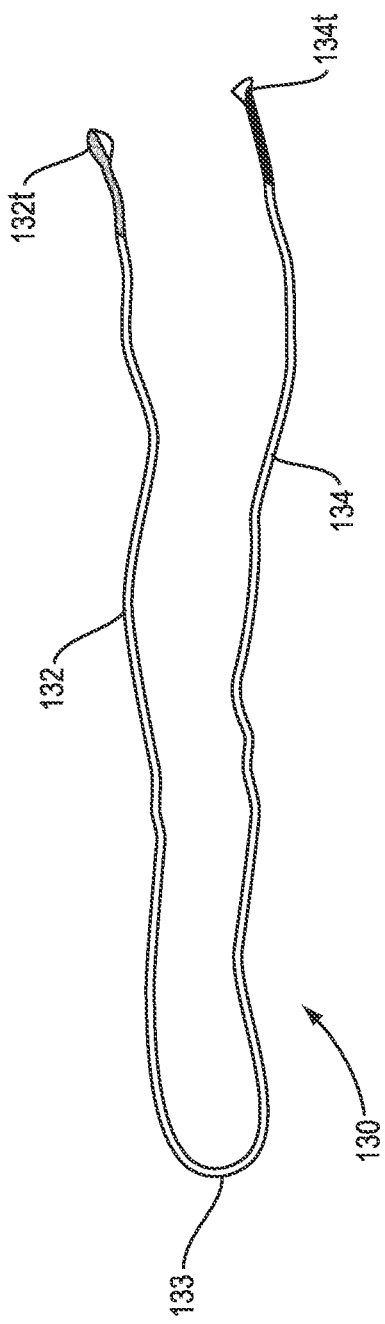

FIGS. 3A-3E illustrate one exemplary method of forming a suture construct 120 having a snare or adjustable loop 122 and a fixed eyelet 124. In this exemplary embodiment, the suture construct 120 is shown being formed from a single length of suture 130. As shown in FIG. 3A, the length of suture 130 can be folded approximately in half such that its opposed first and second terminal ends 132t, 134t are opposed to each other, although such symmetry is by no means required. The folded length of suture 130 may be referred to as having a first portion, limb, or post, identified herein as limb 132, and a second portion, limb, or post, identified herein as post 134, with an apex 133 defining a location at which the limb 132 and post 134 meet. The terms post and limb are used for convenience purposes to help distinguish a first portion of the suture 130 from a second portion of the suture 130, and are by no means limiting as to their use, performance, and purpose.

A loop or opening can be formed in a portion of the suture 130. As shown in FIG. 3B, an overhand knot is used form an overhand knot or loop 136 that defines an opening 138 approximately on a median location of the limb 132. Alternatively, other knots, and other locations for the loop 136 and opening 138, may be used without departing from the spirit of the present disclosure. In embodiments where an anchor is associated with the construct 120, such as a soft anchor 180, it can be associated with any portion of the suture 130 at any time during the manufacturing process. In the illustrated embodiment, the anchor 180 is coupled to the post 134 along a portion of the post. A person skilled in the art will recognize many ways by which the post 134 can be associated with the anchor, including, by way of non-limiting example, by threading the post 134 through one or more portions of the anchor 180. In other embodiments, the anchor may be associated with the construct 120 at some later juncture, including after the construct has been fully formed.

As shown in FIG. 3C, the terminal end 134t of post 134 can be passed through the opening 138 from a first side 120a of the construct 120 to a second side 120b of the construct 120. The first side 120a and the second side 120b can be defined as either side of the opening 138, as shown. In the illustrated embodiment, the terminal end 134t starts on a bottom side of the filament forming the overhand loop 136 (as shown in a top view provided in FIG. 3C, the bottom side being below, or underneath, the filament forming the overhand loop 136) to a top side of the filament forming the overhand loop 136 (as shown in the top view provided in FIG. 3C, the top side being above, or on top of, the filament forming the overhand loop 136) such that as the terminal end 134t enters the opening 138 from the first side 120a, it passes under the filament that forms the overhand loop 136, and as the terminal end 134t exits the opening 138 towards the second side 120b, it passes over the filament that forms the overhand loop 136. Likewise, the terminal end 132t of the limb 132 also exits the opening 138 such that it is disposed on the second side 120b of the construct 120 with it passing over the filament that forms the overhand loop 136, and the portion of the limb 132 that enters the opening 138 passes under the filament that forms the overhand loop 136. A person skilled in the art will recognize that alternative configurations can be used to achieve a similar configuration in which an opening 138 is formed by an overhand loop 136 (or knots and loops) and terminal ends 132t, 134t of a limb 132 and post 134 pass through the opening 138 and extend away from the loop 136 in the same direction. As a result of the illustrated configuration, the snare, or adjustable loop, 122 is formed on the first side 120a of the construct 120. As shown in FIG. 3C, the post 134 is freely slidable through the opening 138 such that a diameter of snare 122 is adjustable as the post 134 is moved with respect to overhand loop 136.

Figure 3D:
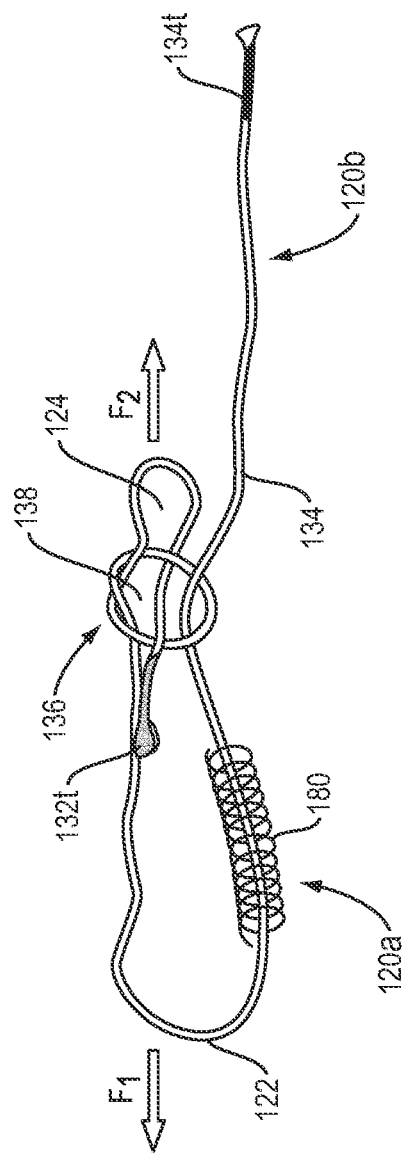
Figure 3E:
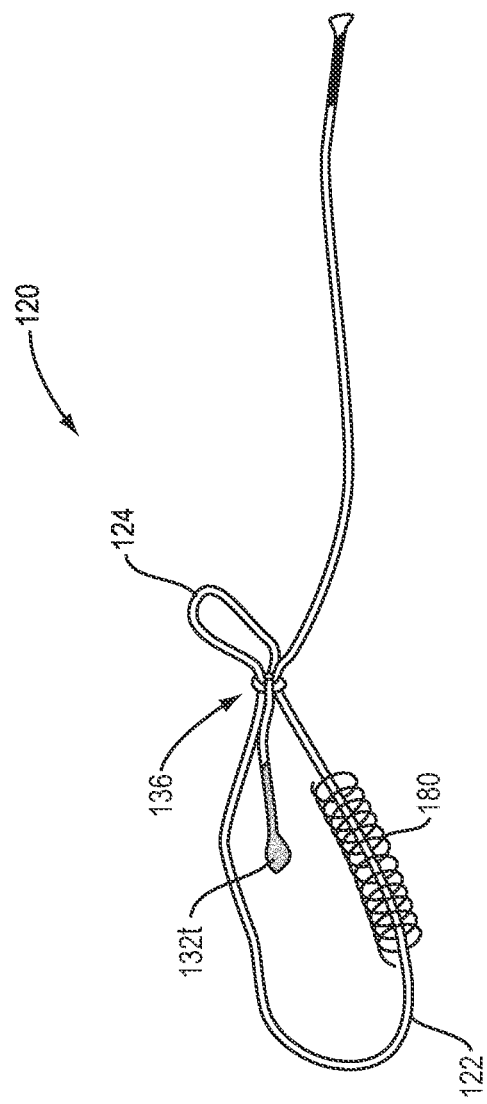

As shown in FIG. 3D, the terminal end 132t of the limb 132 can be threaded through the opening 138 from the second side 120b of the construct 120 to the first side 120a of the construct 120a such that a portion of the limb 132 is disposed within the opening. More particularly, in the illustrated embodiment the terminal end 132t is threaded through the opening 138 by passing it from a bottom side of the filament forming the overhand loop 136 (as shown in a top view provided in FIG. 3D, the bottom side being below, or underneath, the filament forming the overhand loop 136) to a top side of the filament forming the overhand loop 136 (as shown in the top view provided in FIG. 3D, the top side being above, or on top of, the filament forming the overhand loop 136) such that as the terminal end 132t enters the opening 138 from the second side 120b, it passes under the filament that forms the overhand loop 136, and as the terminal end 132t exits the opening 138 towards the first side 120a, it passes over the filament that forms the overhand loop 136. As a result, a portion of the filament closer to the terminal end 132t than the terminal end 134t forms an eyelet 124. With the snare 122 and the eyelet 124 both formed by the filament, the opening 138 can be collapsed or dressed to more fully define each of the snare and eyelet. Collapsing the opening 138 can be achieved in a variety of manners, including but not limited by applying forces to the overhand loop 136 to collapse it, and/or applying a force in a direction $F_1$ to the snare 122, and/or applying a force in a direction $F_2$ to the eyelet 124, as shown in FIG. 3E. The resulting configuration is the construct 120 having the snare 122 with the anchor coupled thereto disposed on one side, as shown the first side 120a, of the dressed overhand loop 136, and the eyelet 124 disposed on the other side, as shown the second side 120b, of the dressed overhand loop 136. A size of the opening defined by the snare 122 can be adjusted by applying tension to the terminal end 132t, and a size of the opening defined by the eyelet 124 can be adjusted by applying tension to the terminal end 134t, although, as discussed below, at least the size of the opening defined by the eyelet 124 can be selectively locked.

While certain exemplary embodiments are illustrated herein, suture constructs 20, 120 can be otherwise configured. For example, while an overhand knot or loop 136 is shown, the opening 138 can be formed by way of alternative knots, loops, or other suture or filament formations known by those skilled in the art to achieve similar functionality. One benefit on an overhand knot 136 is the simplicity and ease of construction, while still providing sufficient strength and adjustability. Moreover, while reference is made to passing certain portions of the limb 132 and the post 134 from the first side 120a to the second side 120b of the construct 120, the limb 132 and the post 134 can be passed through the opening 138 in a variety of ways that result in a configuration that includes the snare 122 and the eyelet 124 disposed on opposite sides of a dressed knot or loop 136.

The suture constructs provided for herein, including but not limited to the constructs 20, 120, or otherwise derivable from the present disclosure, can be operated in a variety of ways. One exemplary embodiment is illustrated in FIGS. 3F-3K. The anchor 180 is not illustrated in FIGS. 3F-3K to make it easier to follow the procedures described below. As provided for herein, the anchor 180 can be included during the performance of the actions illustrated and described with respect to FIGS. 3F-3K, the anchor 180 can be added afterward if desired, or no anchor at all may be provided for in some instances. This is also true for the embodiments described and illustrated with respect to FIGS. 4A-4C.

Figure 3G:
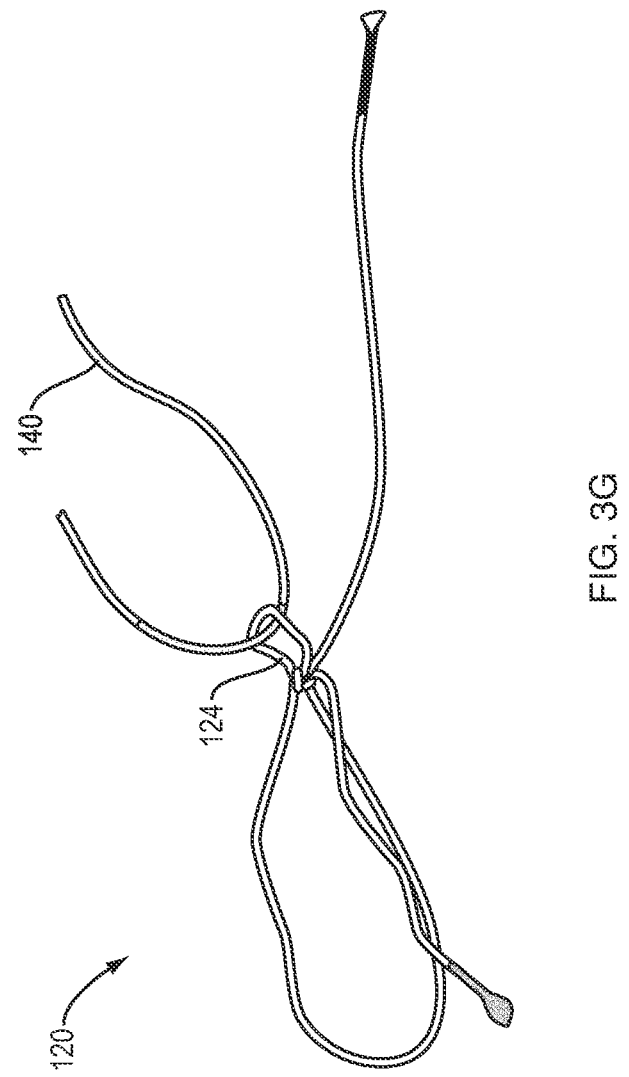

As shown in FIG. 3F, an operative suture 140 can be threaded through the eyelet 124. Alternatively, the operative suture 140 can be threaded through the eyelet at a later step. At this stage the diameter of the eyelet 124 can be varied and is not yet fixed. More particularly, the diameter of the eyelet 124 can be reduced by applying a force on the terminal end 132t of the limb 132, and the diameter of the eyelet 124 can be increased by applying a force on the eyelet 124. As shown between FIGS. 3F and 3G, a force in a direction $F_3$ is applied to the terminal end 132t (FIG. 3F) to reduce the diameter of the eyelet 124 (FIG. 3G). While a person skilled in the art, in view of the present disclosures, will recognize a variety of diameter sizes that can be used in conjunction with the eyelet 124, in some embodiments the diameter of the eyelet 124 can be reduced to a diameter approximately in the range of about 1.5 millimeters to about 15 millimeters, and in some embodiments the diameter can be about 3 millimeters. A variety of factors can includes the size of the diameter of the eyelet 124, including but not limited to the type of procedure being formed, the length and thickness of the filament being used to form the construct 120 and/or the operative suture 140, the type of tissue with which the construct is being used, the amount of tension that will be applied by the operative suture 140 to the eyelet 124 in subsequent use, and/or whether any resistance is desired between the operative suture 140 and the eyelet 124 (as opposed to allowing the operative suture 140 to easily slide with respect to the eyelet 124). Generally the diameter of the eyelet 124 should be kept small so that the implant is not too large, but not so small so as to hinder the ability to use the operative suture 140 and/or lock the eyelet 124—the locking of the eyelet 124 being discussed further below.

Figure 3I:
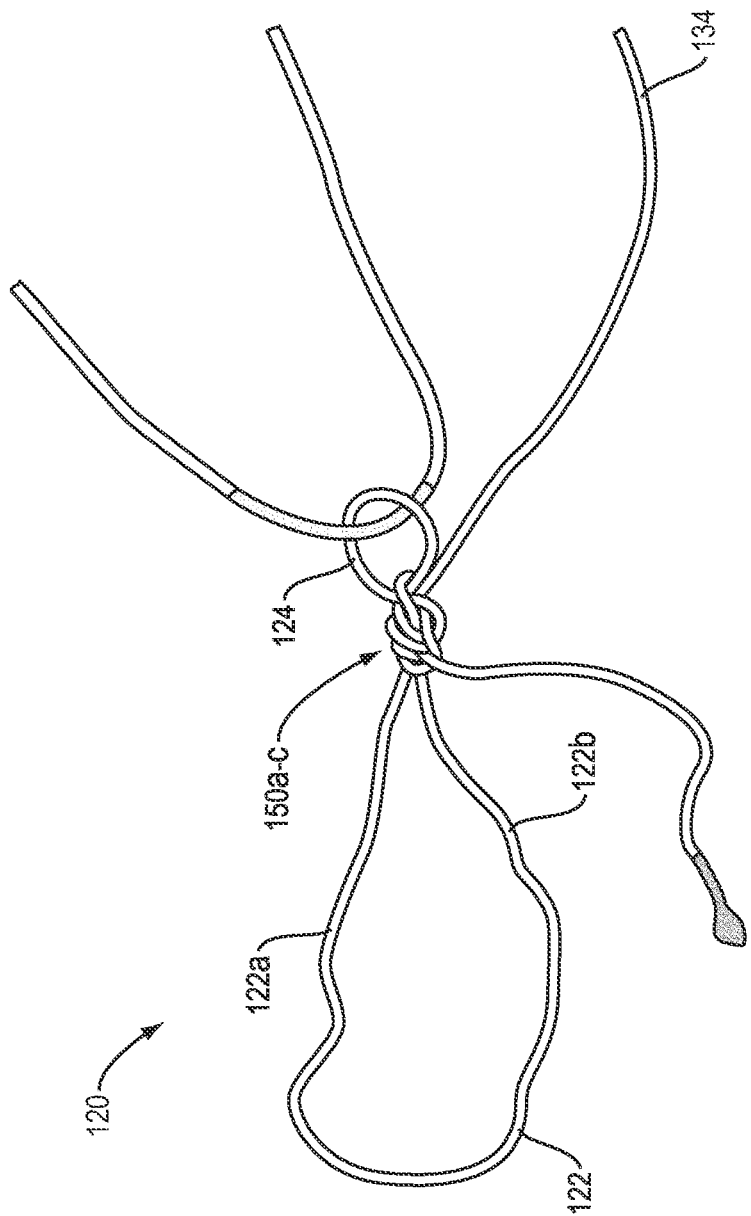

As demonstrated by the illustrations in FIGS. 3H and 3I, one benefit of the construct formation that includes the eyelet 124 as provided is that the diameter of the eyelet 124, while adjustable as described above, can be locked or fixed independent of any fixation of a size of the adjustable loop or snare 122. Turning to FIG. 3H, a first half-hitch knot 150a can be formed (shown in an uncinched configuration) by wrapping the terminal end 132t of the limb 132 around lengths of two portions or limbs 122a, 122b of the snare 122, such portions being proximate to the overhand knot 136. The two limbs 122a, 122b of the snare 122 can function as a post that runs through the first half-hitch knot 150a such that they can both freely slide therethrough. A person skilled in the art will recognize a variety of different knots types that can be used to form the first half-hitch knot 150a, including but not limited to a binding knot, such as a granny knot. A plurality of granny knots can be formed, for example three, to help keep this illustrated configuration intact, such as by helping to keep the post in a substantially straight configuration. Alternatively, the half-hitch knot 150a, and/or additional half-hitch knots, can be formed around one of the two limbs 122a, 122b only.

As shown in FIG. 3I, three half-hitch knots 150a, 150b, and 150c are formed around the two limbs 122a, 122b to fix the diameter of the eyelet 124. In this figure, the first half-hitch 150a is now cinched, with the two additional half-hitch knots 150b and 150c being formed on top of the first half-hitch knot 150a. The post 134 can be slidable through the half-hitch knots 150a, 150b, and 150c, and slidable through the overhand knot 136, such that a diameter of the snare 122 can still be adjusted while the diameter of the eyelet 124 remains fixed. A person skilled in the art, in view of the present disclosures, will recognize the advantageous configuration that results from having a suture construct 120 with a fixed diameter eyelet 124 (and/or selectively fixable as provided for herein) and a variable diameter snare 122.

The suture construct 120 can further include an actuable locking feature, or locking knot 160 (FIG. 3K), which can be used to fix the diameter of the snare 122. This can allow a user to fix the size of the snare 122 upon completion of a procedure to prevent the construct 120 from moving from a desired fixed location and/or from unintentionally moving and/or releasing the soft anchor 180. As described and illustrated below, the operative suture 140 is used to aid in forming the locking knot 160, with the fixed eyelet 124 serving as a limb and the post 134 serving as a post.

Figure 3J:
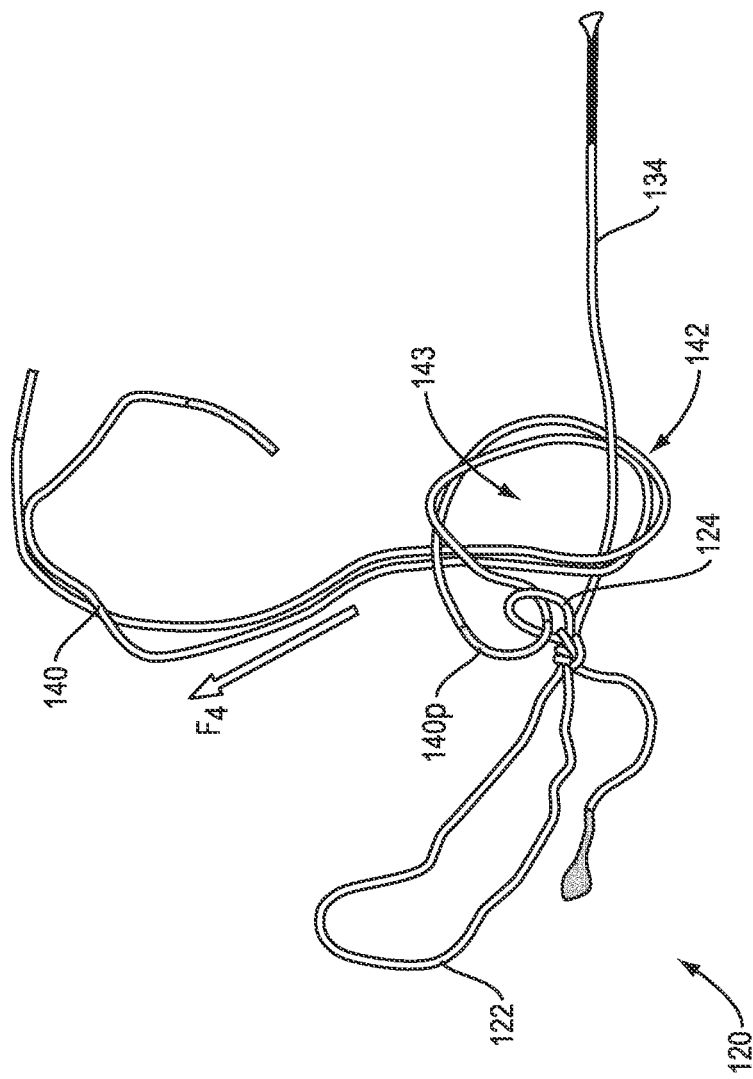

As shown in FIG. 3J, the operative suture 140 can be loosely tied around the post 134, for instance as a half-hitch knot 142, distal to the overhand knot 136. In forming the half-hitch knot 142, the operative suture 140 can be passed from a bottom side of the post 134 (as shown in a top view provided in FIG. 3J, the bottom side being below, or underneath, the post 134) and up over a top side of the post 134 (as shown in the top view provided in FIG. 3J, the top side being above, or on top of, the post 134) before passing below itself to complete the knot 142. The half-hitch knot 142 can be tightened, i.e., a size of an opening 143 formed by the knot 142 can be collapsed, by applying a force in a direction $F_4$ to the operative suture 140, as shown in FIG. 3J. As a result, a proximal portion 140p of the operative suture 140 that is looped through or otherwise disposed in the eyelet 124, pulls the eyelet 124 around the post 134, thereby forming the locking knot 160.

One advantage of the operative suture 140 being threaded through the fixed eyelet 124 is the operative suture 140 can be used to aid in the formation of the locking knot 160 with the fixed eyelet. Alternatively, a person skilled in the art will recognize the locking knot 160 can be formed without using the operative suture 140, for instance by manually manipulating the fixed eyelet 124 and/or using other tools or filaments to manipulate the location of the eyelet 124 with respect to the post 134 in view of the present disclosures.

Figure 3K:
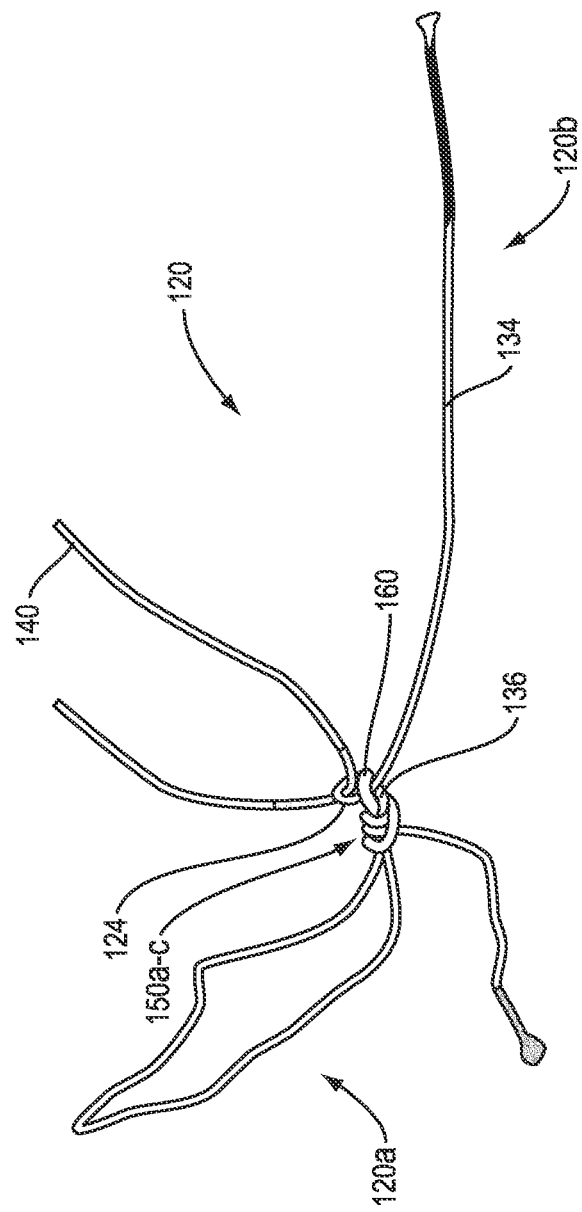

As shown in FIG. 3K, the locking knot 160 is a half-hitch knot that is directly proximate to the overhand knot 136. Alternatively, the locking knot 160 can be formed a distance away from the overhand knot 136. As also shown in FIG. 3K, the overhand knot 136 is directly intermediate the locking knot 160 on the second side 120b of the construct 120 and the three half-hitch knots 150a, 150, and 150c on the first side 120a of the construct 120. In the illustrated embodiment, the post 134 is still slidable through the three half-hitch knots 150a, 150b, 150c, the overhand knot 136, and the locking knot 160 such that the size of the snare 122 can still be adjusted because the locking knot 160 is still in a first, unlocked configuration. Details about how the size of the snare 122 can be adjusted by the post 134, as well as details about how to move the locking knot 160 to the second, locked configuration, are provided with respect to FIGS. 4A-4C.

Figure 4A:
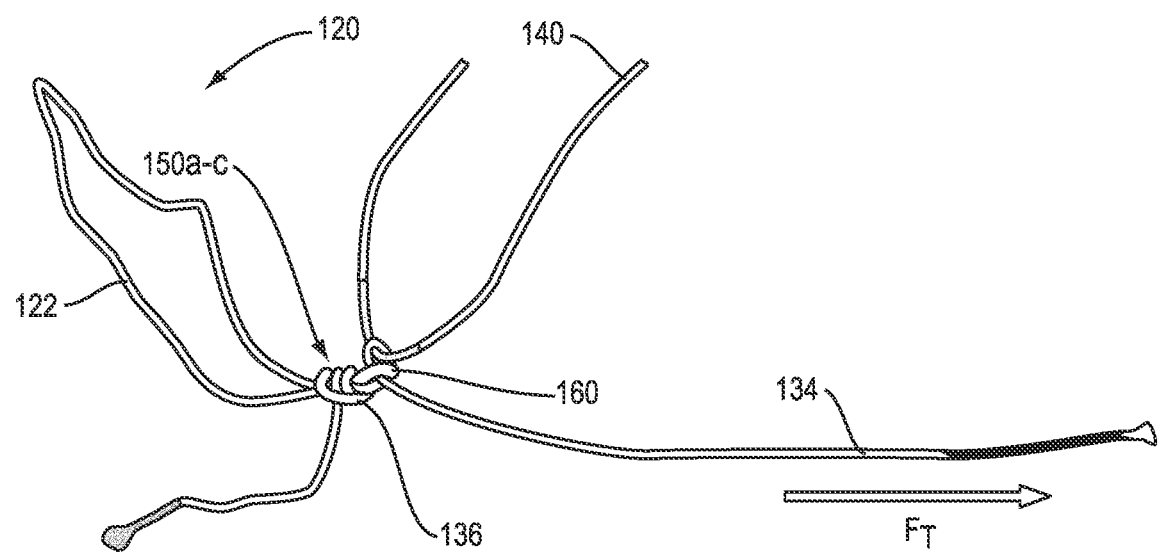
FIGS. 4A-C schematically illustrate one exemplary embodiment of a method of using the suture construct and the operative suture combination of FIG. 3K.
Figure 4B:
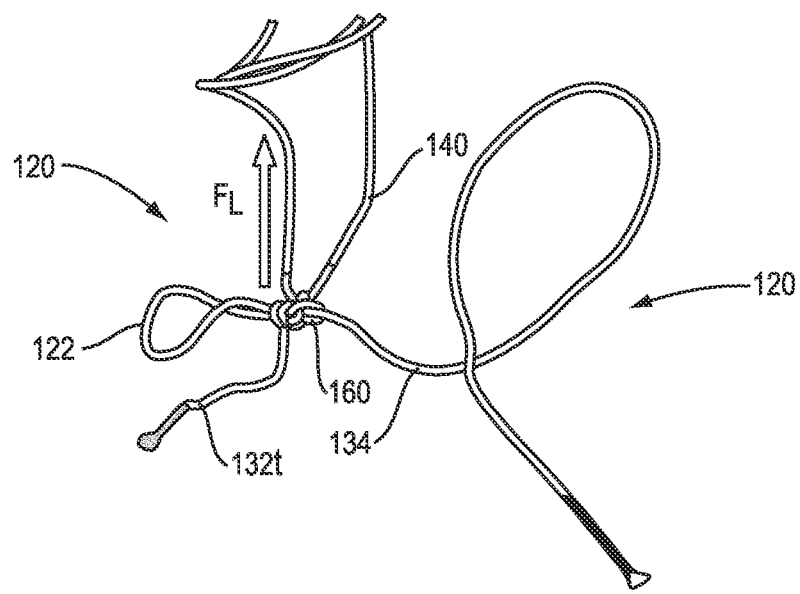

FIG. 4A illustrates the configuration of the construct 120 as it is shown in FIG. 3K, with the post 134 being in a substantially straight line through the knots 150a, 150b, 150c, 136, and 160. As shown, a force in a direction $F_T$ can be applied to the post 134 to slide the post within the locking knot 160 to reduce the diameter of the snare 122, as shown in FIG. 4B. In some embodiments the force in the direction $F_T$ can be approximately in the range of about 5 Newtons to about 150 Newtons, and in some embodiments the force in the direction $F_T$ can be about 20 Newtons. The resulting diameter of the snare 122 can be just about any size known to those skilled in the art, and can depend, at least in part, on the size and shape of other devices, ligaments, implantable bodies, soft anchors, and the like with which the construct 120 is being used, the type of procedure being performed, anatomical conditions, and the preferences of the user. In some surgical embodiments, a diameter of the snare 122 can be adjusted to sizes as large as about 50 centimeters to sizes as small as about 1 millimeter.

Figure 4C:
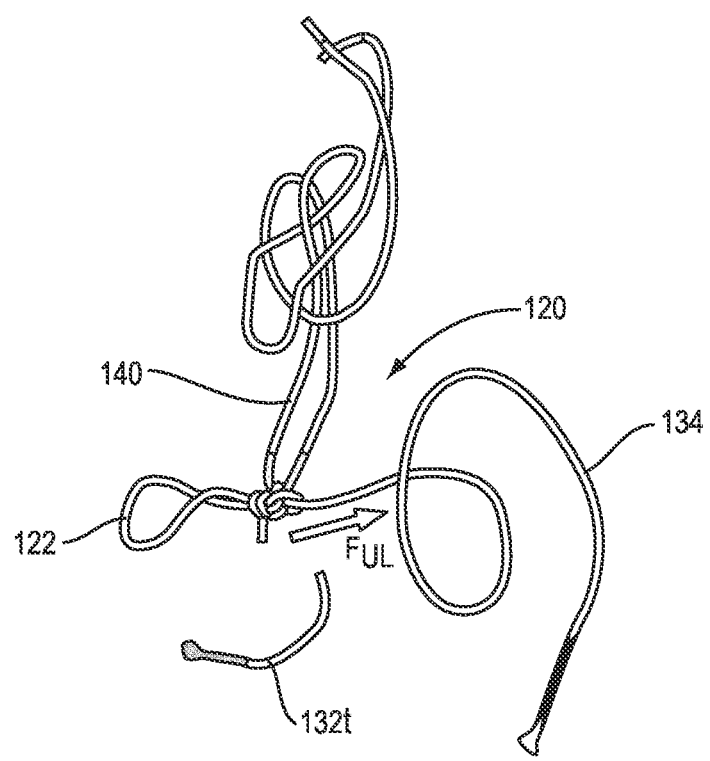

When the diameter of the snare 122 is at the desired size, the locking knot 160 can be actuated from the unlocked configuration (illustrated, for example, in FIG. 4A) to the locked configuration (illustrated, for example, in FIG. 4C). As shown, the locking knot or eyelet 160 is flipped, thus causing it to lock and prevent the post 134 from easily sliding with respect to it. More particularly, as shown in FIG. 4B, a force in a direction $F_L$ can be applied to the operative suture 140, which is disposed through the locking knot 160, to cause the locking knot 160 to flip. By flipping the locking knot 160, it causes the post 134 to be in a relatively tortuous path within the locking knot 160 (i.e., it is no longer in a substantially straight line through the knot 160, or the other knots 150a, 150b, 150c, and 136), placing the locking knot 160 in the second, locked configuration with the diameter of the snare 122 being substantially fixed. Optionally, one or more additional half-hitches can be formed at the locking knot 160 to further secure the diameter of the snare 122.

When the construct 120 is in a locked configuration, a location of a tendon coupled to or otherwise associated with the snare 122 can be fixed at a desired location. Accordingly, during a surgical procedure, placing the construct 120 in the locked configuration can set the desired location of the tendon with respect to the anatomy of the subject. When the construct 120 is in the locked configuration, it can also prevent actuation of a soft anchor coupled thereto because in the locked configuration a size of a diameter of the construct 120 cannot generally be adjusted. A person skilled in the art, in view of the present disclosure, will recognize other configurations and actions that can be performed when the construct 120 is in a locked configuration. Likewise, a number of configurations and actions can be performed when the construct 120 is in an unlocked configuration. In such configurations, a soft suture anchor can be deployed, and/or a location of a tendon can be adjusted by changing a size of the diameter of the construct 120, among other actions that can be performed.

One benefit of the presently designed construct 120 is that it can be moved back from the locked configuration to an unlocked configuration. As shown in FIG. 4C, an unlocking force in a direction $F_{UL}$ can be applied to the post 134 while the remainder of the construct 120 is securely held to flip the locking knot 160 back into the unlocked configuration. Alternatively, or additionally, the operative suture 140 can be used to flip the locking knot 160 back into the unlocked configuration. The ability to selectively lock and unlock the suture construct 120 can provide a number of benefits. For example, it allows a user to selectively and incrementally set and adjust the diameter of the snare 122. Thus, if a user is performing a procedure in which it would be advantageous for the snare 122 diameter to be locked in for one period of time at one diameter but locked in for another period of time(s) at another diameter(s), the present construct would allow the locking knot 160 to be toggled between the unlocked and locked configurations to achieve this flexibility. Further, the lock-unlock capability of the construct 120 allows for errors to be corrected. For example, if the diameter of the snare 122 was set at the wrong size, the locking knot 160 can be moved to the unlocked configuration to fix the snare diameter to the desired size. Likewise, if the size of the snare diameter adjusts during use, for instance because there is some slippage or the filament becomes strained and stretches, the locking knot 160 can be moved to the unlocked configuration to fix the snare diameter to the desired size. Once the locking knot 160 is in the unlocked configuration, the post 134 is able to slide within the locking knot 160 to adjust the diameter of the snare 122.

Advantageously, as the operative suture 140 is slidably disposed within the eyelet 124, and not through a portion of a soft anchor, or other implantable body, the operative suture 140 can be removed after implantation of the suture construct 120. A further advantage of the operative suture 140 being slidably disposed within the eyelet 124 is that the operative suture can be freely adjusted relative to the suture construct 120 to permit the operative suture 140 to be used for other aspect of the procedure, or for additional repairs. These benefits are realized in contrast to suture constructs where implantable bodies, or anchors, are threaded onto the operative suture itself.

A person skilled in the art will recognize that the disclosures provided for with respect to FIGS. 3A-3K can be performed prior to delivering the construct 120 to a surgical procedure room, which is to say they can represent a method of manufacturing a construct for use in a surgical procedure. Alternatively, one or more of the steps can be performed on-site as part of a surgical procedure. Similarly, the disclosures provided for with respect to FIGS. 4A-4C can often be performed on-site as part of a surgical procedure, although, in some instances, at least some aspects can be performed in advance of delivery to the surgical procedure room. For example, in some embodiments the construct 120 can be delivered in a locked configuration with the operative suture 140 already associated with the construct 120 and/or the terminal end 132t trimmed away. The construct 120 can still be selectively unlocked in such an instance, thus achieving the types of benefits provided for by the present disclosures.

While methods of using the suture constructs, or aspects thereof, are provided for above (e.g., the constructs 20, 120), one, more explicit, but non-limiting, exemplary method of using a suture construct implant is provided for with reference back to FIG. 2. A person skilled in the art will recognize such methods can likewise be applicable to other constructs illustrated herein or otherwise derivable from the present disclosure.

As shown, the implant 10 can include the suture construct 20 and a soft anchor 80. The soft anchor 80 can be threaded onto the snare 22, as shown in FIG. 1. Further, the implant 10 can be associated with soft tissue 92 to be attached to bone 94. In the illustrated embodiment, some portion of the construct 20 is passed through the tissue 92, although other techniques for associating an implant 10 with a soft tissue 92 can be used without departing from the spirit of the present disclosure (e.g., wrapping the implant 10 around the tissue 92).

A bore 90 can be formed in a bone 94 using any technique known to those skilled in the art. The implant 10 can then be disposed in the bore 90 so that the implant can be positioned to draw the tissue 92 towards the bone 94 to achieve the repair. As shown, because the anchor 80 is soft, it can be actuated into the anchoring configuration, as shown in FIG. 2. In the illustrated embodiment, the actuation is initiated by reducing the diameter of the snare 22 via application of a force in the direction F to the post 34 (FIG. 1), although a person skilled in the art will recognize a variety of ways by which the soft anchor 80 can be actuated into the anchoring configuration. Likewise, a person skilled in the art will also appreciate that other types of anchors may result in other ways by which the anchor, construct, bone, and tissue are associated. By way of non-limiting example, if the anchor is a hard anchor rather than a soft anchor, the anchor can be implanted in a pre-formed bore or the anchor can be impacted into the bone without a pre-formed bore. The type of anchor, and how the anchor is associated with any of the bone, tissue, or construct, are by no means limiting with respect to the present disclosure. Generally, anchors provided for in conjunction with the present disclosures engage and/or impinge walls of the bore 90, penetrating cancellous bone in some embodiments, and/or are formed such that in their deployed configuration they cannot easily pass out of a bore (e.g., the bore 90) in which they are disposed so that the anchor can be substantially fixed with respect to the bone 94.

As shown in FIG. 2, after the anchor 80 is deployed, a force in a direction $F_L$ can be applied to the operative suture 40, and thus the fixed eyelet 24, to selectively actuate a locking knot 60 according to methods disclosed herein. Knot 60, as shown in FIGS. 1 and 2, can include knots 150a, 150b, 150c, 136, and 160, as shown in FIGS. 3A-4C, among others provided for herein or otherwise derivable therefrom. By way of non-limiting example, the locking knot 60 can be actuated between the unlocked and unlocked configurations in a manner akin to those provided for with respect to the locking knot 160 in conjunction with FIGS. 4A-4C.

Upon completion of a procedure, with the suture construct 10, as well as its components (e.g., the snare 22), fixed at its desired location, as shown in FIG. 2, the operative suture 40 can be removed from the fixed eyelet 24 by sliding it through and out of the fixed eyelet. Further, portions of the post 34 and other excess portions of filament can be trimmed to remove unnecessary filament that may get in the way, cause damage to tissue, etc. Alternatively, either or both the operative suture 40 and the post 34 can remain in place and be used to complete additional actions, such as facilitating capsular repair.

A number of alternative configurations are possible in view of the present disclosures. Some non-limiting examples are provided for in FIGS. 5A, 5B, 6A, 6B, 8A, and 8B.

Figure 5B:
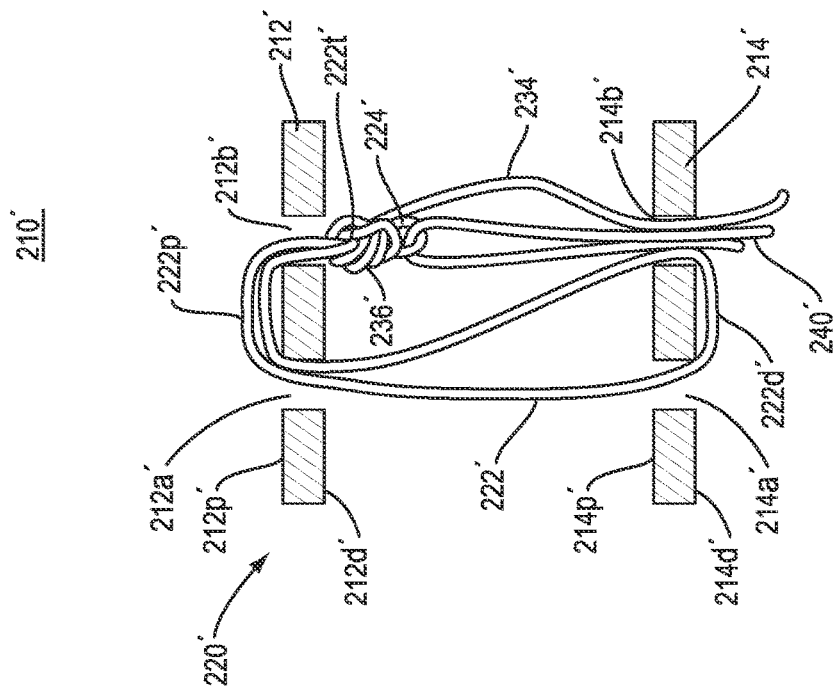
FIG. 5B is another exemplary embodiment of an implant having one exemplary suture construct associated therewith.
Figure 5A:
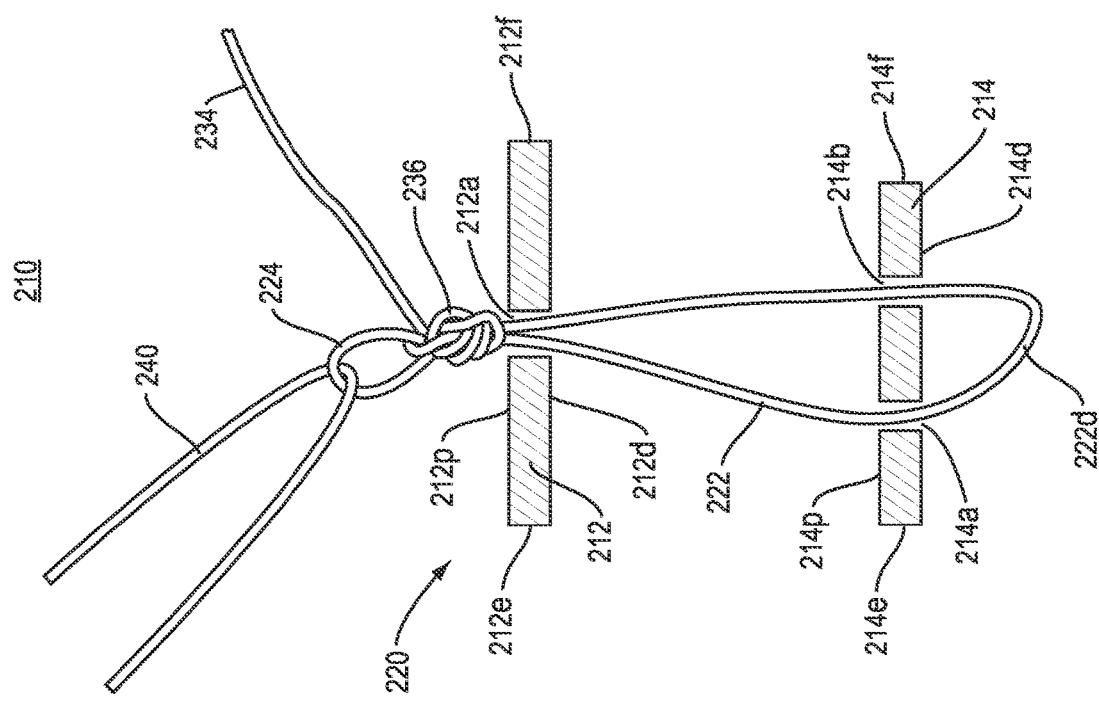
FIG. 5A is one exemplary embodiment of an implant having one exemplary suture construct associated therewith.

FIG. 5A provides for an implant 210 that includes a suture construct 220 that is substantially similar to the suture construct 120 discussed above. For example, as shown, the suture construct 220 includes an adjustable snare loop 222, a fixed eyelet 224, a knot or loop 236, and a post 234, among other features illustrated or otherwise known to be included in view of the present disclosures and knowledge of those skilled in the art. For example, the loop 136 can also be associated with one or more half-hitch knots (akin to knots 150a, 150b, and 150c) and/or a locking knot (akin to knot 160). The post 234 can be used to reduce the diameter of the snare loop 222, as described above with reference to the suture construct 120. An operative suture 240 can be disposed or otherwise associated with the fixed eyelet 224, and can be used or operated in manners provided for herein, such as to selectively lock and unlock movement of the adjustable snare loop 222 via the loop 236 and associated features (e.g., knots).

Just as the implant 110 also included additional components, such as the anchor 80, the implant 210 can also include additional components, such as implantable bodies 212 and 214, also referred to as cortical buttons. The implantable bodies 212 and 214 illustrated in FIG. 5A, as with those illustrated in subsequent figures, are generally schematic in nature. A person skilled in the art will recognize many different sizes, shapes, and configurations of cortical buttons. A body of a cortical button can be generally described as a somewhat rectangular, elongate shape with curved leading and trailing terminal ends 212e, 212f and 214e, 214f (curves not illustrated in this schematic illustration, but understood by a person skilled in the art as one design option). One or more through-holes 212a and 214a, 214b can be formed in the bodies 212 and 214. In the illustrated embodiment, the implantable body 212 includes one through-hole 212a that is approximately centrally disposed along a length of the body 212, while the implantable body 214 includes two through-holes 214a, 214b that are approximately equally spaced along a length of the body from a center of the body 214. Diameters of the through-holes 212a, 214a, 214b can be the same or different on either or both of the bodies 212, 214. A thickness of each of the bodies 212, 214 can be defined by the distance between a proximal surface 212p and 214p and a distal surface 212d and 214d of the respective bodies, and a width (not visible in FIG. 5A) can be defined by a distance between the two sidewalls disposed on a same side of a length of the respective bodies 212, 214.

The suture construct 220 can be associated with the implantable bodies 212 and 214 by passing or otherwise disposing portions thereof through the through-holes 212a and 214a, 214b. More particularly, as shown, the loop 222 can be thread or otherwise passed or disposed through the through-hole 212a between the proximal side 212p of the first (as shown upper) body 212 and the distal side 212d of the body 212. The diameter of the through-hole 212a can be less than a diameter of the resulting knot 236 such that the knot 236 is maintained on the proximal side 212p of the upper body 212, thus forming an interference fit between the knot 236 and body 212. The loop 222 can likewise be thread or otherwise passed or disposed through the through-holes 214a, 214b. More particularly, as shown, a distal end 222d of the loop 222 can be thread through the through-holes 214a, 214b between the proximal side 214p of the second (as shown lower) body 214 and the distal side 214d of the body 214.

A person skilled in the art, in view of the present disclosures, will understand that the procedure for associating the bodies 212, 214 with the construct 220 can be performed in a variety of different manners, such as by threading the bodies 212, 214 onto the construct 220 prior to forming the loop 236, prior to dressing the loop 236, etc. This is likewise true for the other combinations of constructs (e.g., constructs 220', 220'', 220''', 320, 320') and bodies (212', 214', 212'', 214'', 212''', 214''', 312, 314, 312', 314') provided for herein, or combinations that can be derived in view of the present disclosures. The suture construct implant 210 can be used in any of the variety of procedures as described below with regards to alternative suture construct implants 210', 210'', 210''', 310, and 310', as well as other procedures known or otherwise derivable in view of the present disclosures. Likewise, the other implants provided for herein (e.g., implants 210', 210'', 210''', 310, and 310') can be used in any of the variety of procedures described herein, as well as other procedures known or otherwise derivable in view of the present disclosures.

FIG. 5B provides for an alternative configuration of an implant 210' that allows a knot 236', as well as a fixed eyelet 224', to be disposed underneath an implantable body 212', as shown between the implantable bodies 212' and 214'. The configuration and operability of a suture construct 220', adjustable snare loop 222', fixed eyelet 224', knot or loop 236', and post 234' are generally akin to their counterpart components of the implant 210 of FIG. 5A. Likewise, the configuration and operability of implantable bodies 212' and 214' are also generally akin to their counterpart implantable bodies 212 and 214, except, for example, that the first (as shown upper) implantable body 212' includes two through-holes 212a', 212b' instead of one through-hole 212a. The second (as shown lower) implantable body 214 includes two through-holes 214a', 214b', just like the implantable body 214.

The suture construct 220' can be associated with the implantable bodies 212' and 214' by passing or otherwise disposing portions thereof through the through-holes 212a', 212b' and 214a', 214b'. The illustrated configuration is similar to that of the implant 210 of FIG. 5A in that a distal end 222d' of the loop 222' can be thread through the through-holes 214a', 214b' between a proximal side 214p' of the second body 214' and a distal side 214d' of the second body 214'. The additional through-hole 212b' in the first implantable body 212' can allow a proximal end 222p' of the loop 222' to be thread or otherwise passed or disposed through both through-holes 212a', 212b' between the proximal side 212p' of the first body 212' and the distal side 212d' of the first body 212'. As shown, any or all of a terminal end 222t' of the loop 222' proximate to the knot 236', the knot 236', and the eyelet 224' can be disposed distal of the distal side 212d' of the first body 212'. In the illustrated embodiment, the terminal end 222t' of the loop 222', the knot 236', and the eyelet 224' are all disposed distal of the distal side 212d' of the first body 212' and proximal of the proximal side 214p' of the second body 214'. In some instances, at least a portion of the terminal end 222t' of the loop 222' may be disposed within the through-hole through which the loop 222' is passed and/or proximal of that through-hole. Disposing some or all of these portions below the distal side 212d' of the first body 212' can help prevent damage to tissue (e.g., inflammation, irritation) that can be caused by those portions contacting the tissue when those portions are disposed proximal of the proximal side 212p' of the first body 212'. The illustrated configuration can also help keep such portions intact, such as by preventing accidental cutting of the knot 236' when trimming suture tails, such as the post 234'. As shown, the post 234' and/or an operative suture 240' associated with the eyelet 224' can extend through the through-hole 214b', although other configurations are possible, including but not limited to having one or both of them pass through any of the through-holes 212a', 212b', 214a', 214b', and/or having one or both of them not extend through any of the through-holes 212a', 212b', 214a', 214b'. Another alternative implant 210" is shown in FIG. 6. The implant 210" includes a suture construct 220" which can be substantially similar to the suture constructs 120, 220 discussed above. For example, as shown, the suture construct 220" include an adjustable snare loop 222" a fixed eyelet 224" a knot or loop 236", and a post 234", among other features illustrated or otherwise known to be included in view of the present disclosures and knowledge of those skilled in the art. For example, the loop 236" can also be associated with one or more half-hitch knots (akin to knots 150a, 150b, and 150c) and/or a locking knot (akin to knot 160). The post 234' can be used to reduce the diameter of the snare loop 222" as described above with reference to the suture construct 120. An operative suture 240" can be disposed or otherwise associated with the fixed eyelet 224", and can be used or operated in manners provided for herein, such as to selectively lock and unlock movement of the adjustable snare loop 222" via the loop 236" and associated features (e.g., knots).

Similar to the implants 110, 210, and 210', the implant 210" can include additional components, such as implantable bodies 212" and 214", again alternately referred to as cortical buttons. The implantable bodies 212" and 214" illustrated in FIG. 6 are schematic in nature. A person skilled in the art will recognize various sizes, shapes, and configurations that can be used as the implantable bodies 212" and 214". Similar to the implantable body 212, the first (as shown upper) implantable body 212" includes a through-hole 212a" that is approximately centrally disposed along a length of the body 212" Differing from the illustrated implantable bodies 214, 214", the second (as shown lower) implantable body 214" includes just one through-hole, a through-hole 214a" the through-hole being approximately centrally disposed along a length of the body 214" Diameters of the through-holes 212a" 214a" can be the same or different on either or both of the bodies 212" 214" The bodies 212" 214" can also have thicknesses and widths, as described above with respect to the bodies 212, 214. And locations of the through-holes 212a" 214a" can be varied, such as one or both not being approximately centrally disposed along a length of their respective bodies 212" 214".

The suture construct 220" can be associated with the implantable bodies 212" and 214" by passing or otherwise disposing portions thereof through the through-holes 212a" and 214a". More particularly, as shown, the loop 222" can be thread or otherwise passed or disposed through the through-hole 212a" between a proximal side 212p" of the first body 212" and a distal side 212d" of the body 212". The diameter of the through-hole 212a" can be less than a diameter of the resulting knot 236" such that the knot 236" is maintained on the proximal side 212" of the upper body 212" thus forming an interference fit between the knot 236" and body 212". While in the embodiment illustrated in FIG. 5A the loop 222 was likewise disposed through the body 214 via one or more through-holes (e.g., the through-holes 214a and 214b), for the implant 210" the loop 222" is coupled to or otherwise associated with the lower body 214" by way of an attachment suture 241". More particularly, as shown, the attachment suture 241", is coupled to a distal end 222d" of the loop 222", for instance by passing a portion of the attachment suture 241" through a portion of the loop 222", and the attaching suture is thread or otherwise passed or disposed through the through-hole 214a" between a proximal side 214p" and a distal side 214d" of the body 214". A knot 242" disposed on the attachment suture 241" as shown on its distal end 240d", although other locations are possible, can have a diameter that is larger than a diameter of the through-hole 214a" such that the knot 242" is maintained on the distal side 214d" of the body 214", thus forming an interference fit between the knot 242" and body 214". As a result, a location of the loop 222" is maintained with respect to the body 214d" when a force in an upward direction, i.e., towards the upper body 212", is applied to a portion of the implant 210' Similar to the implants 110, 210, and 210', the implant 210' can be used in any variety of procedures as described below, as well as other procedures known or otherwise derivable in view of the present disclosures.

Figure 6B:
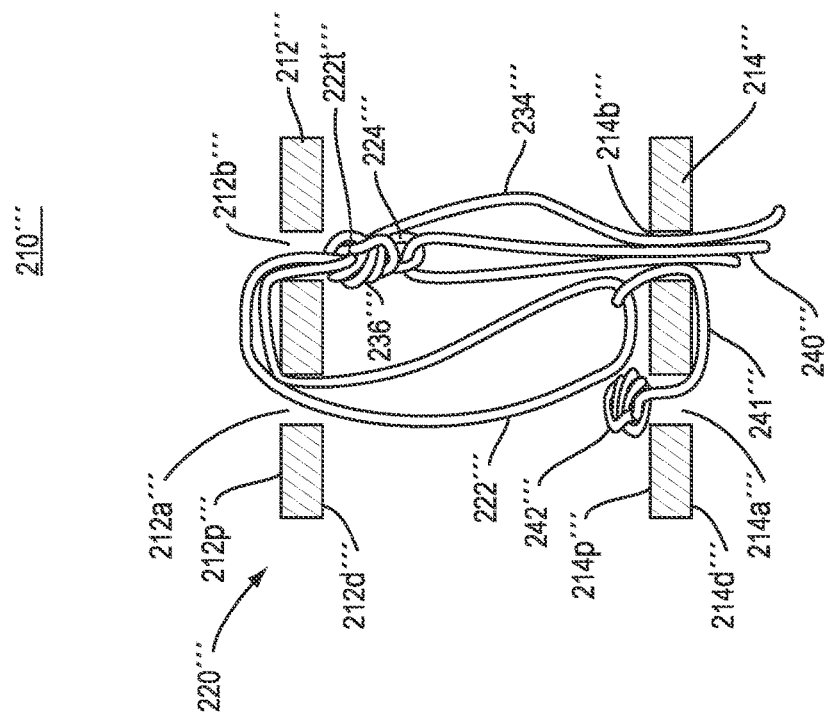
FIG. 6B is still another exemplary embodiment of an implant having one exemplary suture construct associated therewith.
Figure 6A:
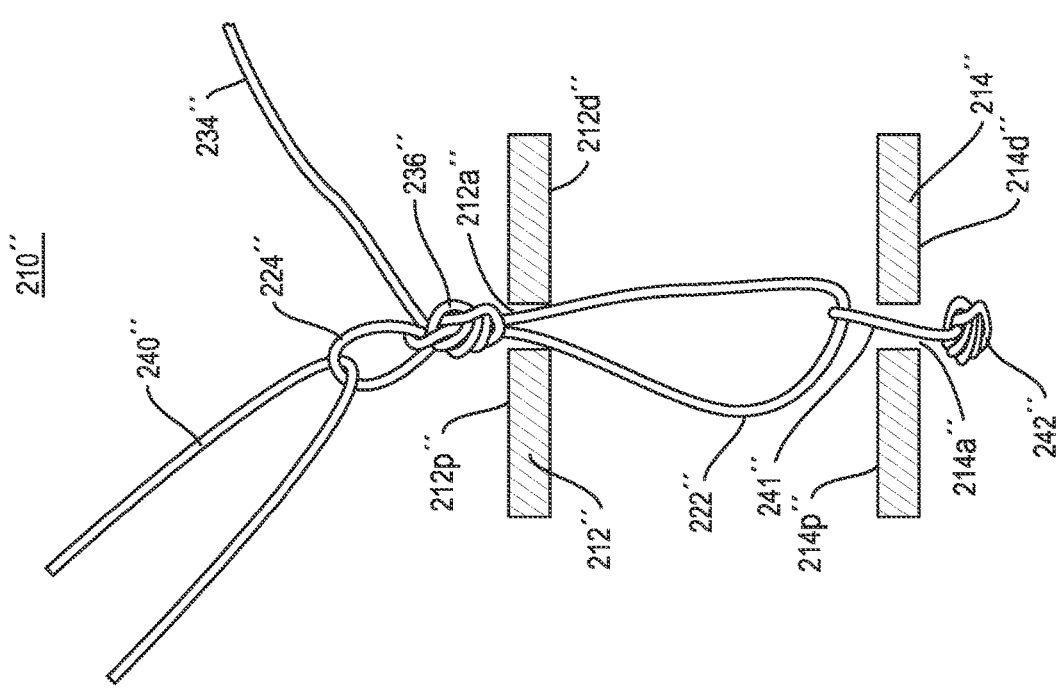
FIG. 6A is yet another exemplary embodiment of an implant having one exemplary suture construct associated therewith.

FIG. 6B provides for an alternative configuration of an implant 210''' that combines some of the benefits described with respect to the implant 210' of FIG. 5B with some of the benefits described with respect to the implant 210" of FIG. 6A. The configuration and operability of a suture construct 220''', adjustable snare loop 222''', fixed eyelet 224''', knot or loop 236''', post 234''', attachment suture 241''', and knot 242''' are generally akin to their counterpart components of the implants 210, 210', and 210" of FIGS. 5A, 5B, and 6A, respectively. Further, the configuration and operability of implantable bodies 212''' and 214''' are generally akin to their counterpart implantable bodies 212' and 214, 214', with the both the first (as shown upper) implantable body and the second (as shown lower) implantable body each having two through-holes 212a''', 212b''' and 214a''', 214b''', respectively.

The suture construct 220''' can be associated with the implantable bodies 212''' and 214''' by passing or otherwise disposing portions thereof through the through-holes 212a''', 212b''', 214a''', 214b'''. The illustrated configuration of FIG. 6B with respect to the first implantable body 212''' is similar to that of the implant 210' of FIG. 5B in that a terminal end 222t''' of the loop 222''', the knot 236''', and the eyelet 224''' can all be disposed distal of a distal side 212d''' of the first body 212'''. Likewise, the illustrated configuration of FIG. 6B with respect to the second implantable body 214''' is similar to that of the implant 210' of FIG. 5B in that the terminal end 222t''' of the loop 222''' the knot 236''', and the eyelet 224''' can all be disposed proximal of a proximal side 214p''' of the second body 214''', and further, the operative suture 240''' and the post 234''' can extend through the through-hole 214b'''. A further benefit illustrated with respect to the implant 210''' of FIG. 6B is that the attachment suture 240''' can be passed through the through-hole 214a''' such that the knot 242''' is disposed proximal of the proximal side 214p''' of the second body. This location can be beneficial for the same reasons described above as to why disposing the knot 236' and eyelet 224' distal of the distal side 212d' of the implantable body 212' is beneficial with respect to the implant 210' of FIG. 5B. As shown, in the illustrated embodiment, the knot 242''' can be disposed distal of the distal side 212d''' of the implantable body 212'''.

Figure 7:
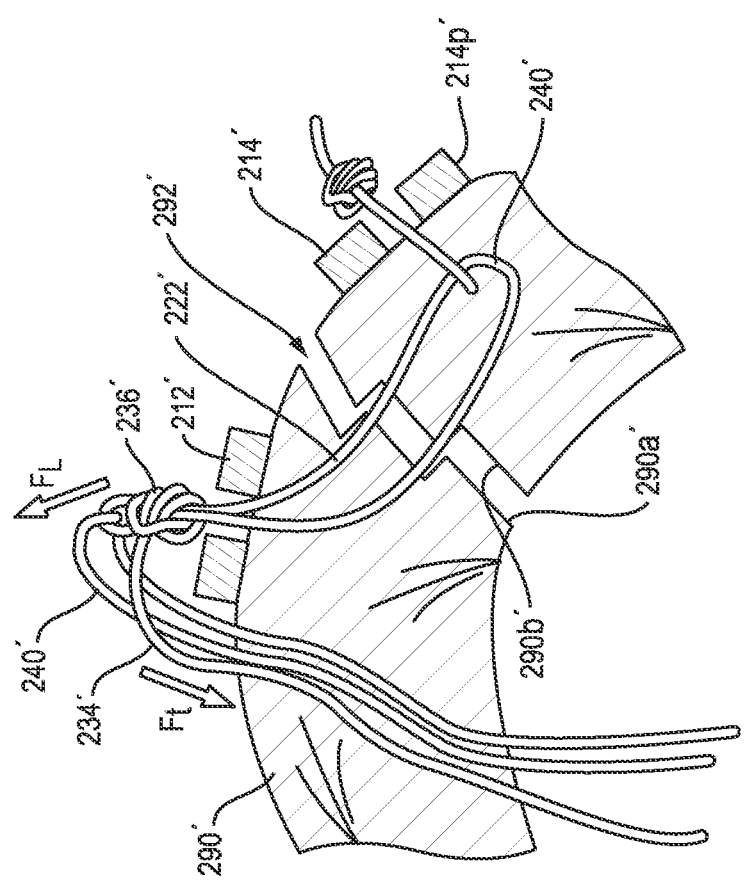
FIG. 7 is a schematic illustration of the implant and suture construct of FIG. 6 being used in a meniscal repair.

FIG. 7 provides for one non-limiting example of a surgical procedure that can be performed using the implant 210'. A person skilled in the art, in view of the present disclosures, will understand variations of the described procedure, as well as other procedures, that can be performed using the implant 210'. Likewise, a person skilled in the art, in view of the present disclosures, will understand other implants, including but not limited to the implants described herein or otherwise derivable from the present disclosures, and/or variations thereof, that can be used in conjunction with procedure described with respect to FIG. 7.

FIG. 7 is illustrative of a meniscal tear 292' involving tissue 290a' and 290b'. The tissue 290a', 290b' can be prepared according to accepted surgical techniques and the implant 210' can be introduced to the surgical site. In the illustrated embodiment, the implant 210' is situated such that the lower cortical button 214' is disposed proximate to the tissue 290b', with its proximal side 214p' disposed against the tissue 290b', the upper cortical button 212' is disposed proximate to the tissue 290a', with its distal side 212d' disposed against the tissue 290a', and the suture construct 220' passing between the cortical buttons 212', 214' such that it passes through portions of the tissue 290a', across the tear 292', and through portions of the tissue 290b'. A person skilled in the art will recognize many different techniques that can be performed to achieve this configuration, including but not limited to passing one or both cortical buttons 212', 214' through portions of the tissue 290a', 290b' and/or first passing the construct 220' through the tissue 290a', 290b' and then associating the buttons 212', 214' with the tissue 290a', 290b' so as not to pass any buttons through the tissue. Likewise, although the construct 220' is shown passing through portions of the tissue 290a', 290b', in other configurations the construct 220' can be wrapped around, or be otherwise associated with the tissue 290a', 290b', in lieu of or in addition to passing the construct 220' through the tissue 290a', 290b. The key to this set-up is that the implant 210' is associated with both tissues 290a' and 290b' such that the construct 220' can be operable to draw the tissues together.

Once the implant 210' is associated with the tissue 290a', 290b', the implant 210' can be operated to draw the tissue 290a', 290b' together, thereby closing the tear 292'. This can be accomplished, for example, by applying a force in a direction $F_t$ on the post 234' to reduce the diameter of the snare 222'. The surgeon can hold the knot 236', and/or the upper cortical button 212', in place during the tightening of the snare 222' to provide a counter force to the force in the direction $F_t$ to prevent the implant 210' from being pulled out of the tissue. The counter force can be applied, for example, by a knot pusher (not shown), or by other tools and/or techniques known to those skilled in the art, e.g., applying the counter force by hand if access at the surgical site exists. Once the tissue 290a', 290b' is brought into contact to close the tear 292', the implant 210' can be actuated to fix the diameter of the snare 222'. As discussed above with respect to the implant 110, the implant 210' can be locked by the application of a locking force in a direction $F_L$ to an operative suture 240', which is disposed in the eyelet 224' of the implant 210'. By applying the locking force in the direction $F_L$ to the operative suture, the locking knot, which is part of the knot 236', is actuated and thereby changes the path of the post 234' from a straight path through the knot 236' to a tortuous path. While the post 234' is in the tortuous path through the knot 236', the diameter of the snare 222' is substantially fixed, thereby retaining the tissue 290a', 290b' together to allow for the tear 292' to heal according to accepted medical techniques. Once the snare 222' of the implant 210' has been fixed, the operative suture 240' can be removed from the eyelet 224' and the post 234' can be trimmed. Alternatively, the operative suture 240' and the post 234' can remain to aid in additional repairs, such as facilitating capsular repair.

Figure 9:
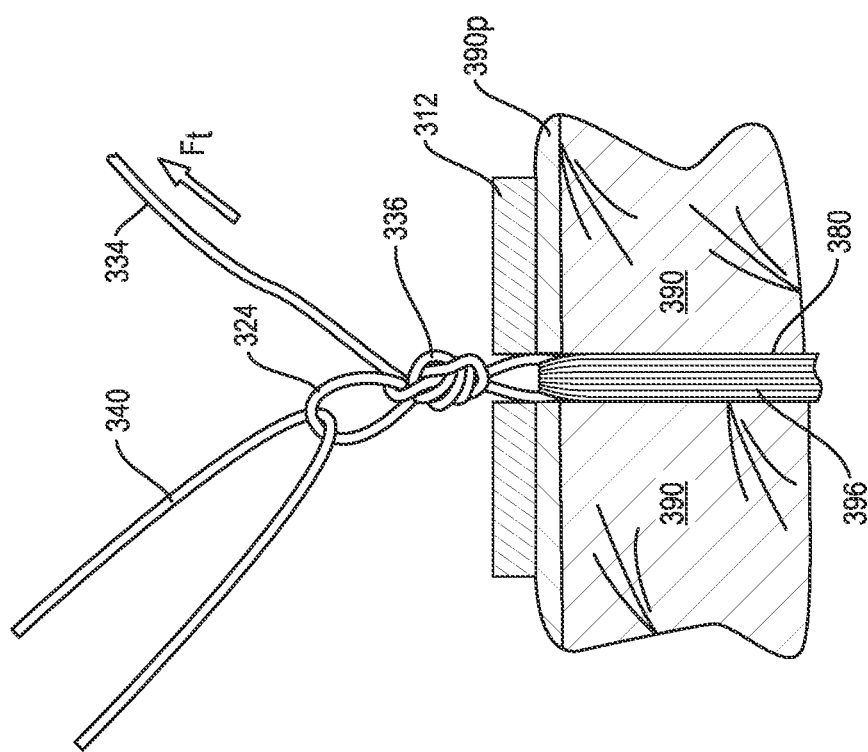
FIG. 9 is a schematic illustration of the implant and suture construct of FIG. 8A being used in a collateral ligament repair.

Yet another alternative implant 310 is illustrated in FIGS. 8A and 9. The implant 310 includes a suture construct 320 and implantable body or cortical button 312, which can be substantially similar to the suture constructs 120, 220, 220' and the implantable bodies 212, 212', and 214' discussed above. Other configurations of suture constructs and implantable bodies, including other configurations described above or otherwise derivable in view of the present disclosures, can also be used. In the illustrated embodiment, the suture construct 320 includes an adjustable snare loop 322, a fixed eyelet 324, a knot or loop 336, and a post 334, among other features illustrated or otherwise known to be included in view of the present disclosures and knowledge skilled in the art. For example, the loop 336 can also be associated with one or more half-hitch knots (akin to knots 150a, 150b, and 150c) and/or a locking knot (akin to knot 160). The post 334 can be used to reduce the diameter of the snare loop 322, as described above with reference to the suture construct 120. An operative suture 340 can be disposed or otherwise associated with the fixed eyelet 324, and can be used or operated in manners provided for herein, such as to selectively lock and unlock movement of the adjustable snare loop 322 via the loop 336 and associated features (e.g., knots).

Further, similar to the implants 110, 210, and 210', the implantable body 312 is schematically illustrated, and a person skilled in the art will recognize various sizes, shapes, and configurations that can be used as the implantable body 312. In the illustrated embodiment, the implantable body 312 includes a through-hole 312a that is approximately centrally disposed along a length of the body 312, the hole 312a extending between a proximal side 312p and a distal side 312d of the body 312. The suture construct 320 can be coupled to or otherwise associated with the implantable body 312 using techniques provided for herein or otherwise known to those skilled in the art. As shown, a proximal end 322p of the snare loop 322 is disposed proximate to the knot 336 and the implantable body 312, with the knot 336 being disposed at or proximal of the proximal side 312p with a major diameter of the knot 336 being greater than a diameter of the through-hole 312a so that a location of the construct 320 with respect to the implantable body 312 can be maintained.

A tendon 396 can be associated with the adjustable snare loop 322, as shown at a distal end 322d of the snare loop 322. The tendon 396 can be coupled to or otherwise associated with the adjustable snare loop 322 using any techniques known to those skilled in the art, including but not limited to passing the tendon 396 through an opening defined by the snare such that a portion of the tendon 396 is disposed on the distal end 322 of the loop 322, with other portions of the tendon 396 extending on either side of the loop 322 as shown. In alternative, non-limiting embodiments, a portion of the snare loop 322 can be thread through a portion of the tendon 396 and the loop 322 can be manipulated such that it wraps around a portion of the tendon 396. In the illustrated embodiment, the tendon 396 can be freely slidable with respect to the loop 322, although in other embodiments it can be fixed relative to the snare loop 332.

FIG. 8B provides for an alternative configuration of an implant 310' that, similar to the implants 210' and 210''', allows a knot 336', as well as a fixed eyelet 324', to be disposed underneath an implantable body 312'. The configuration and operability of a suture construct 320', adjustable snare loop 322', fixed eyelet 324', knot or loop 336', and post 334' are generally akin to their counterpart components of the implant 310 of FIG. 8A, and thus their counterpart components of the implants 210, 210', 210''', and 210'''. Likewise, the configuration and operability of implantable body 312' is generally akin to its counterpart implantable bodies 212' and 212''', with the implantable body 312' having two through-holes 312a', 312b'.

The suture construct 320' can be associated with the implantable body 312' in similar ways as described above, with one resulting configuration being one in which a terminal end 322t' of the loop 322', the knot 336', and the eyelet 324' being disposed distal of a distal side 312d' of the implantable body 312'. AS discussed above with respect to the loop 222', in some instances, at least a portion of the terminal end 322t' of the loop 322' may be disposed within the through-hole through which the loop 322' is passed and/or proximal of that through-hole. As shown, an operative suture 340' and the post 334' can likewise be disposed distal of the distal side 312d' of the implantable body 312', such sutures extending distally therefrom. The configuration of the suture construct 320' having the knot 336' and the eyelet 324' disposed distal of the distal side 312d' of the implantable body 312', i.e., underneath the body 312', allows sutures to be tensioned in a way that causes the implant 310' to operate in a pulley-like manner. This "pulley" movement can cause the repair to become taut as tension continues to be applied to the implant 310', for example by applying tension to the post 334'. This is true at least for the other configurations provided above in which a knot and eyelet are disposed distal of a distal side of an implantable body, such as for the implants 210' and 210''' of FIGS. 5B and 6B, respectively. Still further, in embodiments that include multiple implantable bodies, such as the implants 210' and 210''' of FIGS. 5B and 6B, respectively, tension can also be derived between the plurality of implantable bodies. Further, similar to the description above with respect to the implant 310, a tendon 396' can be associated with the adjustable snare loop 322', as shown at a distal end 322d' of the snare loop 322'. The tendon 396' can be coupled to or otherwise associated with the adjustable snare loop 322' using any techniques known to those skilled in the art, including but not limited to those provided above.

FIG. 9 provides one exemplary embodiment of the implant 310 being used in a surgical repair procedure that includes a bone 390 and graft 396. Many different types of surgical procedures can be performed using the implant 310, but in some exemplary embodiments it can be an ACL repair. The repair can be prepared according to accepted surgical techniques, such as forming a bone bore 380 in the bone 390, the bore 380 being a space into which the graft 396 is implanted.

The implant 310 can be passed through the bore 380 until the implantable body 312 is located above a proximal surface 390p of the bone 390. A person skilled in the art will recognize a number of ways by which the implant 310 can be advanced through the bore 380, but in one embodiment a force in a direction FB can be applied to the operative suture 340 to advance the implant 310, and thus the graft 396, in a similar direction, up through the bore 380. In such instances, the eyelet 324 can have been manipulated into a locked configuration so that application of the force in the direction FB to the operative suture 340 does not accidentally cause a diameter of the eyelet 324 and/or the suture loop 322 to change. Alternatively, the eyelet 324 can remain in the unlocked configuration, as application of force to the operative suture 340 does not necessarily cause a diameter of the eyelet 324 and/or suture loop 322 to change. Further, in some instances, it may be desirable to both advance the implant 310 through the bore 380 while also, simultaneously, adjusting a length of the suture loop 322, for instance by applying a force in a direction $F_t$ to the post 334.

After the body 312 has passed through the bore 380, proximal of the proximal surface 390p of the bone, the body 312 can be manipulated such that one of its surfaces, e.g., the proximal or distal surfaces 312p, 312d, rests against the proximal surface 390p of the bone 390. In the illustrated embodiment, the distal surface 312d rests against the proximal surface 390p. The graft 396 can be moved to its desired position with respect to the bone 390 and bore 380 by changing a diameter of the snare loop 322. For example, a force in a direction $F_t$ can be applied to the post 334 to reduce the diameter of the adjustable snare 322, thereby advancing the tendon 396 towards the proximal surface 390p of the bone 390. A person skilled in the art will recognize that adjusting a diameter of the snare loop 322 to move the graft 396 can occur at any time during a surgical procedure.

Once the tendon 396 is at the desired location for the procedure, the knot 336 can be actuated to lock the diameter of the snare 322 by application of a locking force on the operative suture 340, as described elsewhere herein with respect to other embodiments. Further, the implant 310 can be locked in the same manner as discussed above with suture constructs 20, 120, 220, 220'. Optionally, the operative suture 340 can be removed and/or the post 334 can be trimmed to remove excess suture once the snare 322 is in the desired configuration and the procedure is otherwise completed. Alternatively, the operative suture 340 and the post 334 can be left in place and used to perform additional repairs or serve other purposes at or near the surgical site, such as facilitating capsular repair.

The type of graft-bone repair provided for with respect to FIG. 9 is applicable to many different types of surgical procedures, including but not limited to an ACL repair and meniscal repairs. The systems, devices, and methods provided for herein can be incorporated into various ACL and meniscal repairs without departing from the spirit of the present disclosure. Some non-limiting examples of ACL repair procedures are described in U.S. Pat. No. 9,387,065, the content of which is incorporated by reference herein in its entirety. Further, a person skilled in the art will recognize a number of modifications that can be made to the various repair procedures discussed herein, or otherwise derivable from the present disclosure, without departing from the spirit of the disclosure. By way of one non-limiting example, although the embodiments herein illustrate the suture construct 20, 120, 220, 220', 320 passing through tissue at one location, in other embodiments, it can pass through two or more locations and/or two or more tissues. By way of further non-limiting example, the suture construct 20, 120, 220, 220', 320 can be coupled to tissue using a variety of techniques, for instance wrapping a portion of the suture construct 20, 120, 220, 220', 320 around the tissue. Still further, a person having skill in the art will recognize that the order of at least some of the method steps provided herein can be altered without departing from the spirit of the present disclosure.

Additionally, the procedures discussed are just some forms of procedures that can be performed in conjunction with systems, devices, and methods disclosed herein. A person skilled in the art will recognize a number of other ways that the disclosed systems, devices, and methods can be used in various other configurations and types of surgical procedures. For instance, the systems, devices, and methods disclosed herein can easily be adapted to be used in conjunction with three or more components, such as multiple tissues and a bone or three or more soft tissues. Some non-limiting examples of other systems, devices, assemblies, constructs, and surgical procedures with which the present systems, devices, and methods can be used are described in in U.S. Pat. Nos. 9,060,763, 9,095,331 and 9,345,468, the content of each which is incorporated by reference herein in each's entirety if not already incorporated by reference above.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A method of using a suture repair construct, comprising:
    tying a first limb of a suture repair construct about a portion of an adjustable loop of the suture repair construct to set a size of an opening defined by an eyelet of the suture repair construct, the size of the opening defined by the eyelet being adjustable prior to tying the first limb of the suture repair construct about the portion of the adjustable loop;
    tying the eyelet about a second limb of the suture repair construct to form a lockable knot, the second limb of the suture repair construct being operable to control a size of an opening defined by the adjustable loop and the second limb being configured to slide within the lockable knot after the eyelet is tied about the second limb;
    disposing an operative suture in the eyelet such that a portion of the operative suture is disposed on opposed sides of the eyelet and
    manipulating the operative suture to tie the eyelet about the second limb of the suture repair construct to form the lockable knot.

2. The method of claim 1, further comprising tensioning the first limb of the suture repair construct to collapse the size of the opening defined by the eyelet prior to tying the first limb of the suture repair construct about a portion of the adjustable loop of the suture repair construct to set a size of the opening defined by the eyelet.

3. The method of claim 1, further comprising tensioning the second limb of the suture repair construct to collapse the size of the opening defined by the adjustable loop after tying the eyelet about the second limb of the suture repair construct to form the lockable knot.

4. The method of claim 1, further comprising coupling the suture repair construct to a suture anchor.

5. The method of claim 4, wherein the suture anchor further comprises a soft anchor configured to be fixated in bone and formed of a flexible construct, the soft anchor having an unstressed configuration with a first length and a first diameter and an anchoring configuration with a second length that is less than the first length and a second diameter that is greater than the first diameter.

6. The method of claim 5, further comprising:
    inserting the soft anchor in a bone;
    threading at least a portion of the operative suture through a portion of tissue;
    tensioning the second limb to move the anchor from the first configuration to the second configuration; and
    tensioning the eyelet to move the lockable knot from a first, unlocked configuration to a second, locked configuration.

7. The method of claim 6, wherein tensioning the eyelet to move the lockable knot from the first, unlocked configuration to the second, locked configuration causes a tendon coupled to the adjustable loop of the suture repair construct to be substantially fixed at a desired location.

8. The method of claim 6, further comprising manipulating the eyelet to move the lockable knot from the second, locked configuration to the first, unlocked configuration.

9. The method of claim 8, wherein manipulating the eyelet to move it from the second, locked configuration to the first, unlocked configuration allows a diameter of the adjustable loop of the suture repair construct to be adjusted after previously having been fixed when in the locked configuration.

10. A method of using a suture repair construct, comprising:
    tying a first limb of a suture repair construct about a portion of an adjustable loop of the suture repair construct to set a size of an opening defined by an eyelet of the suture repair construct, the size of the opening defined by the eyelet being adjustable prior to tying the first limb of the suture repair construct about the portion of the adjustable loop;
    tying the eyelet about a second limb of the suture repair construct to form a lockable knot, the second limb of the suture repair construct being operable to control a size of an opening defined by the adjustable loop and the second limb being configured to slide within the lockable knot after the eyelet is tied about the second limb;

threading at least a portion of an operative suture through a portion of tissue, the operative suture having at least one limb disposed within the lockable knot;

tensioning the second limb to adjust a diameter of the adjustable loop; and tensioning a limb of the operative suture to flip the lockable knot from a first, unlocked configuration to a second, locked configuration to substantially fix the diameter of the adjustable loop.

11. The method of claim 10, further comprising applying an unlocking force to one or more of the first limb or the second limb of the suture repair construct to flip the lockable knot from the second, locked configuration to the first, unlocked configuration.

12. The method of claim 11, wherein a remainder of the suture repair construct is securely held while the unlocking force is being applied.

13. The method of claim 11, further comprising adjusting the diameter of the adjustable loop by sliding the second limb within the lockable knot.

14. The method of claim 10, further comprising:
disposing the operative suture in the eyelet such that a portion of the operative suture is disposed on opposed sides of the eyelet; and
manipulating the operative suture to tie the eyelet about the second limb of the suture repair construct to form the lockable knot.

15. The method of claim 10, further comprising coupling the suture repair construct to a suture anchor.

16. The method of claim 15, wherein the suture anchor further comprises a soft anchor configured to be fixated in bone and formed of a flexible construct, the soft anchor having an unstressed configuration with a first length and a first diameter and an anchoring configuration with a second length that is less than the first length and a second diameter that is greater than the first diameter.

17. The method of claim 16, further comprising:
inserting the soft anchor in a bone;
threading at least a portion of the operative suture through a portion of tissue;
tensioning the second limb to move the anchor from the first configuration to the second configuration; and
tensioning the eyelet to move the lockable knot from a first, unlocked configuration to a second, locked configuration.

18. The method of claim 17, wherein tensioning the eyelet to move the lockable knot from the first, unlocked configuration to the second, locked configuration causes a tendon coupled to the adjustable loop of the suture repair construct to be substantially fixed at a desired location.

19. The method of claim 17, further comprising manipulating the eyelet to move the lockable knot from the second, locked configuration to the first, unlocked configuration.

20. The method of claim 19, wherein manipulating the eyelet to move it from the second, locked configuration to the first, unlocked configuration allows a diameter of the adjustable loop of the suture repair construct to be adjusted after previously having been fixed when in the locked configuration.

21. A method of using a suture repair construct, comprising:
tying a first limb of a suture repair construct about an intermediate portion of the first limb of the suture repair construct to form a loop;

passing a distal-most end of the first limb through the loop to define an eyelet of the suture repair construct having an opening, a size of the opening defined by the eyelet being adjustable prior to tying the first limb of the suture repair construct about the portion of an adjustable loop; and tying the eyelet about a second limb of the suture repair construct to form a lockable knot, the second limb of the suture repair construct being operable to control a size of an opening defined by the adjustable loop and the second limb being configured to slide within the lockable knot after the eyelet is tied about the second limb.

22. The method of claim 21, further comprising:
disposing an operative suture in the eyelet such that a portion of the operative suture is disposed on opposed sides of the eyelet; and
manipulating the operative suture to tie the eyelet about the second limb of the suture repair construct to form the lockable knot.

23. The method of claim 21, further comprising tensioning the first limb of the suture repair construct to collapse the size of the opening defined by the eyelet prior to tying the first limb of the suture repair construct about a portion of the adjustable loop of the suture repair construct to set a size of the opening defined by the eyelet.

24. The method of claim 21, further comprising tensioning the second limb of the suture repair construct to collapse the size of the opening defined by the adjustable loop after tying the eyelet about the second limb of the suture repair construct to form the lockable knot.

25. The method of claim 21, further comprising coupling the suture repair construct to a suture anchor.

26. The method of claim 25, wherein the suture anchor further comprises a soft anchor configured to be fixated in bone and formed of a flexible construct, the soft anchor having an unstressed configuration with a first length and a first diameter and an anchoring configuration with a second length that is less than the first length and a second diameter that is greater than the first diameter.

27. The method of claim 26, further comprising:
inserting the soft anchor in a bone;
threading at least a portion of the operative suture through a portion of tissue;
tensioning the second limb to move the anchor from the first configuration to the second configuration; and
tensioning the eyelet to move the lockable knot from a first, unlocked configuration to a second, locked configuration.

28. The method of claim 27, wherein tensioning the eyelet to move the lockable knot from the first, unlocked configuration to the second, locked configuration causes a tendon coupled to the adjustable loop of the suture repair construct to be substantially fixed at a desired location.

29. The method of claim 27, further comprising manipulating the eyelet to move the lockable knot from the second, locked configuration to the first, unlocked configuration.

30. The method of claim 29, wherein manipulating the eyelet to move it from the second, locked configuration to the first, unlocked configuration allows a diameter of the adjustable loop of the suture repair construct to be adjusted after previously having been fixed when in the locked configuration.

\* \* \* \* \*